United States Patent [19]
Hasegawa et al.

[11] Patent Number: 5,432,543
[45] Date of Patent: Jul. 11, 1995

[54] ENDOSCOPIC IMAGE PROCESSING DEVICE FOR ESTIMATING THREE-DIMENSIONAL SHAPE OF OBJECT BASED ON DETECTION OF SAME POINT ON A PLURALITY OF DIFFERENT IMAGES

[75] Inventors: Jun Hasegawa, Hino; Nagaaki Oyama, Kawasaki; Masahiro Yamaguchi, Tokyo; Tetsuo Nonami, Tama, all of Japan

[73] Assignee: Olympus Optical Co., Ltd., Tokyo, Japan

[21] Appl. No.: 37,004

[22] Filed: Mar. 25, 1993

[30] Foreign Application Priority Data
Mar. 5, 1992 [JP] Japan .................................. 5-045563
Mar. 27, 1992 [JP] Japan .................................. 4-071299

[51] Int. Cl.⁶ .......................... H04N 7/18; A61B 1/04
[52] U.S. Cl. .......................................... 348/45; 348/65; 348/699
[58] Field of Search ...................... 348/45, 65, 136, 74, 348/71, 699; 382/6, 1, 17; 359/107; 128/660.03, 660.06

[56]  References Cited
U.S. PATENT DOCUMENTS

| 4,573,191 | 2/1986 | Kidode et al. ........................ 382/1 |
| 4,895,431 | 1/1990 | Tsujiuchi et al. ..................... 382/6 |
| 4,903,204 | 2/1990 | Dobbins, III .................... 364/413.21 |
| 4,935,810 | 6/1990 | Nonami et al. ...................... 348/45 |
| 4,980,762 | 12/1990 | Heeger et al. . |
| 5,105,466 | 4/1992 | Tsujiuchi et al. ..................... 382/1 |
| 5,150,254 | 9/1992 | Saitou .................................. 348/65 |
| 5,153,721 | 10/1992 | Eino et al. ........................... 348/74 |
| 5,282,030 | 1/1994 | Nishimura et al. ................. 358/527 |

FOREIGN PATENT DOCUMENTS
63-246716 10/1988 Japan .
1-64625 3/1989 Japan .

Primary Examiner—Tommy P. Chin
Assistant Examiner—A. Au
Attorney, Agent, or Firm—Armstrong, Westerman, Hattori, McLeland & Naughton

[57]  ABSTRACT

The position of the same point on each of the images of a single object formed by the imaging means of an endoscope is detected, and shift maps between the respective images are formed using the detected positions. Each of the imaging positions of the imaging means is estimated from the shift maps, and a relative shape of the object is then estimated from the imaging positions. Since a relative shape of the object is estimated using the correlation between the respective images, a relative shape of the object can be estimated even when not only the imaging means but also the object are moved. An absolute shape of the object can also be estimated using a length as a reference value.

56 Claims, 22 Drawing Sheets

TEMPLATE IMAGE

REFERENCE IMAGE

ENDOSCOPIC IMAGE PROCESSING DEVICE FOR ESTIMATING THREE-DIMENSIONAL SHAPE OF OBJECT BASED ON DETECTION OF SAME POINT ON A PLURALITY OF DIFFERENT IMAGES

BACKGROUND OF THE INVENTION

1. Field of the Invention

The present invention relates to an endoscopic image processing device for estimating a three-dimensional shape of an object by employing correlations between the positions of the same point on a plurality of images of the same object.

2. Description of the Related Art

When the relative arrangement of the imaging means disposed with overlap in a visual field is known, various methods are known which estimate the shape of an object from the images formed, i.e., for estimating the shape from stereo-images.

In recent years, some methods have also been proposed for determining a three-dimensional structure from information about the movement of an object. The methods employ the technique of estimating the relative movement of imaging means from a plurality of images.

All methods use as original information the assumption that a plurality of images at the same point on an object have a positional relation.

Various methods have also been proposed for detecting the positions of the same point on images of an object. The method of extracting a structure by extracting segments is effective for an artificial object because angles and contour components of the object are frequently clear. However, this method cannot be easily applied to a general natural image. Although a density gradient method which is frequently used for time series images produces good results when the apparent movement of an object between images is small and when the image quality is good, imaging conditions are greatly limited.

A block matching method is generally used in which a target point on an image and the circumference thereof are selected as reference areas, and correlation operation is performed between the reference areas and the areas selected from images of a search object to obtain as corresponding points positions having the maximum correlation value. Although the block matching method produces relatively stable results when the image has a clear texture, the method sometimes causes error in detection of a corresponding point when the texture is unclear.

The block matching method also has an intrinsic fault in that when an object is a solid body and contains, for example, a boundary within a block on the background, in which the detection results obtained are unreliable. When the images formed by a plurality of imaging means exhibit large differences in shape and size due to the inclination of the object surfaces with respect to the imaging means or differences in distance between the object and the imaging means, the results obtained are also unreliable.

Problems with respect to the estimation of a three-dimensional shape include problems with respect to occlusion and matching of the estimated results. Particularly, there are portions which cannot be seen from the imaging means side and are not imaged, or portions which are imaged by only one of the imaging means on estimation from stereoscopic images, and handling of these portions is a problem.

When the number of the imaging means is increased, the number of regions to be imaged is inevitably increased, and the number of portions which cannot be seen from the imaging means side is thus decreased. Particularly, when the positions of the imaging means are not known, or when estimation cannot be correctly made, however, the matching between the images is difficult.

Most of the conventional methods have been proposed for images of an artificial object. Alternatively, the effects of the problems inevitably produced when a method is devised for images of a natural object have been removed or decreased by providing some assumptions. Thus it cannot be said that the conventional methods are sufficient for practical use.

Examples of images to which the conventional methods cannot be easily applied and which exhibit a large practical value when being actually employed include images obtained from a bioendoscope.

In an endoscope which permits an affected part in a body cavity to be observed and, if required, the affected part to be treated using a treatment apparatus by inserting a long thin insertion portion into the body cavity without the need for discission, since the size of the tip portion must be minimized in view of the function, it is impossible to incorporate members other than members necessary for a doctor to observe or treat the affected part.

Several proposals have already been made for determining the shape of an object in a trans-endoscopic manner. Examples of proposals include a method of projecting pattern light or the like to a observation object (Japanese Patent Laid-Open No. 64-64525), and a method of providing a compound eye at the tip portion of an endoscope (Japanese Patent Laid-Open No. 63-244011). Since both methods require the tip portion of the endoscope or a light source portion to have a specific structure, the device used is increased in size and complicated, thereby causing difficulties in general use.

Japanese Patent Application No. 62-168791 filed by the same assignee discloses a method of estimating the shape of an object from a plurality of images obtained by moving the tip of an endoscope by manual operation, and a measurement mechanism for measuring the movement amount of the tip moved by the operation. This method can estimate the shape of an object without losing the function of the present endoscope.

However, when this method is used, particularly, for an endoscope used in a living body, the relative movement of the object to the tip of the endoscope, which is caused by a difference in the imaging time phase, cannot be disregarded. In addition, although the precision of the measurement mechanisms is not insufficient in view of the resolution of the imaging means and the like, it is difficult to say that the precision is sufficient.

In addition, since the bioendoscope is mainly used for observing the image of a mucous membrane without clear angles, contours and textures, the detection of corresponding points remarkably causes problems, and it is necessary to take some measures against the problems of the detection results of the corresponding points employed for estimation.

As described above, there is no method or device for estimating the shape of an object which is capable of stably producing good results of estimation of the positions of imaging means and the shape of the object even if applied to a natural image having no clear characteristic point, for example, an endoscopic image, and which has no need for changing the device (increasing the size of the device or the like) to an extent which affects the intrinsic observation function.

SUMMARY OF THE INVENTION

An object of the present invention is to provide an endoscopic image processing device which is capable of estimating the shape of an object with good precision from a plurality of images obtained by imaging the same object.

Another object of the present invention is to provide an endoscopic image processing device which is capable of estimating the shape of an object with good precision from a plurality of images obtained by imaging the same object without providing additional measurement mechanisms on imaging means.

An endoscopic image processing device of the present invention comprises an endoscope provide with imaging means, position detection means for detecting the positions of the same point on a plurality of images of the same object formed by the imaging means, position estimating means for estimating the imaging positions of the imaging means from the positions of the same point on the images, shape estimating means for estimating a three-dimensional shape of the object from the imaging positions estimated by the position estimating means, and display means for displaying the three-dimensional shape estimated. The device is thus capable of detecting the positions of the same point on a plurality of images obtained by imaging the same object while moving the position of the imaging means little by little, estimating the relative position of the imaging means on the basis of the detected position thereof, and estimating the shape of the object by repeated processing for improving the estimation precision according to demand.

BRIEF DESCRIPTION OF THE DRAWINGS

FIGS. 1 to 16 relate to a first embodiment of the present invention, in which:

FIG. 1 is a drawing of the entire configuration of an electronic endoscopic system in accordance with the first embodiment;

FIG. 2 is a block diagram illustrating the block configuration of an electronic endoscopic device;

FIG. 3 is a block diagram illustrating the configuration of an image processing device;

FIG. 4 is a block diagram illustrating an image processing device comprising a CPU;

FIG. 5 is a block diagram illustrating an image processing device comprising hardware;

FIG. 6 is a block diagram illustrating the configuration of a recording device;

FIG. 10 is a drawing explaining the step of calculating shift maps from a two-dimensional image data sequence;

FIG. 11 is a flowchart showing the specific step of calculating a shift map and repeatedly processing the movement vector;

FIG. 12 is a drawing explaining the coordinate system of central projection;

FIG. 13 is a drawing explaining the rotation axis and the rotation vector;

FIG. 14 is a drawing explaining the fact that three vectors are on the same plane;

FIG. 16 is a flowchart showing the processing of repeated estimation;

DESCRIPTION OF PREFERRED EMBODIMENTS

Figure 1:
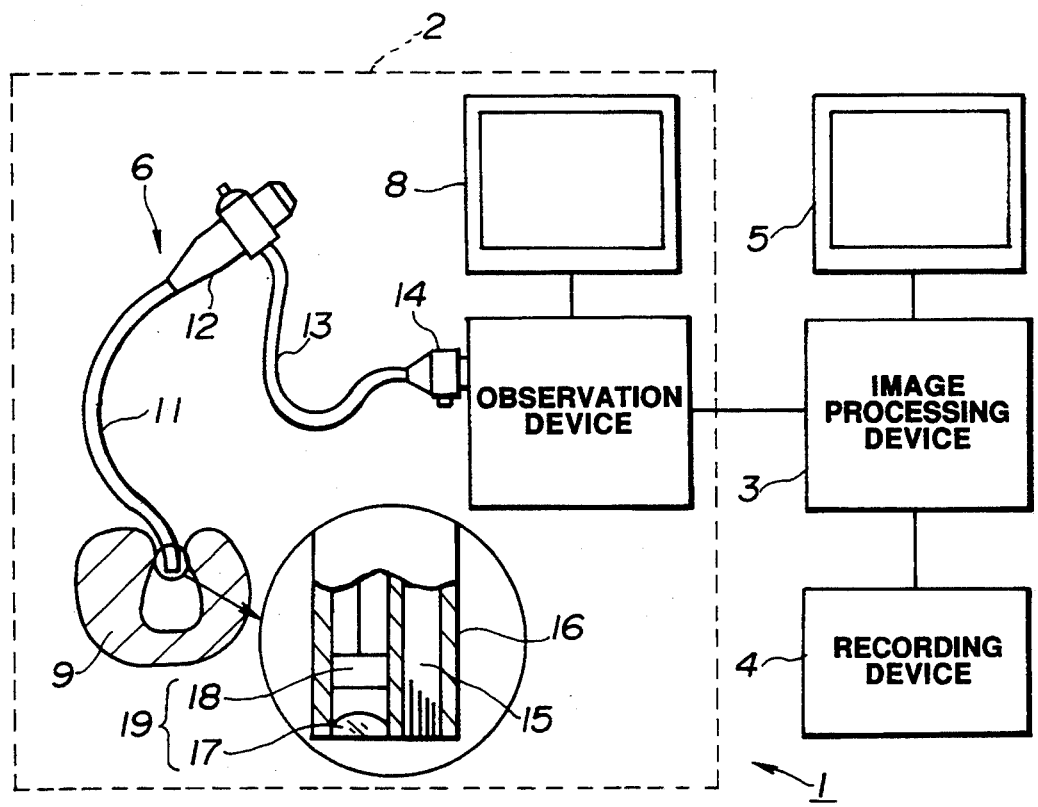

As shown in FIG. 1, an endoscopic system 1 comprises an electronic endoscopic device 2 provided with imaging means, an image processing device 3 for processing images to estimate a three-dimensional shape of an affected part or the like on the basis of the images formed according to a first embodiment, a recording device 3 for recording images, and a monitor 5 for displaying the image processed.

The electronic endoscopic device 2 comprises an electronic endoscope 6, an observation device 7 containing a light source portion 7A (refer to FIG. 2) for supplying illuminating light to the electronic endoscope 6 and a signal processing portion 7B for processing signals of the imaging means, and an observation monitor 8 for displaying the image signal output from the observation device 7.

The electronic endoscope 6 comprises a long thin insertion portion 11 to be inserted into a living body 9, an operating portion 12 formed at the rear end of the insertion portion 11, and a universal cable 13 extended from the operating portion 12. A connector 14 provided at an end of the universal cable 13 can be connected to the observation device 7.

Figure 2:
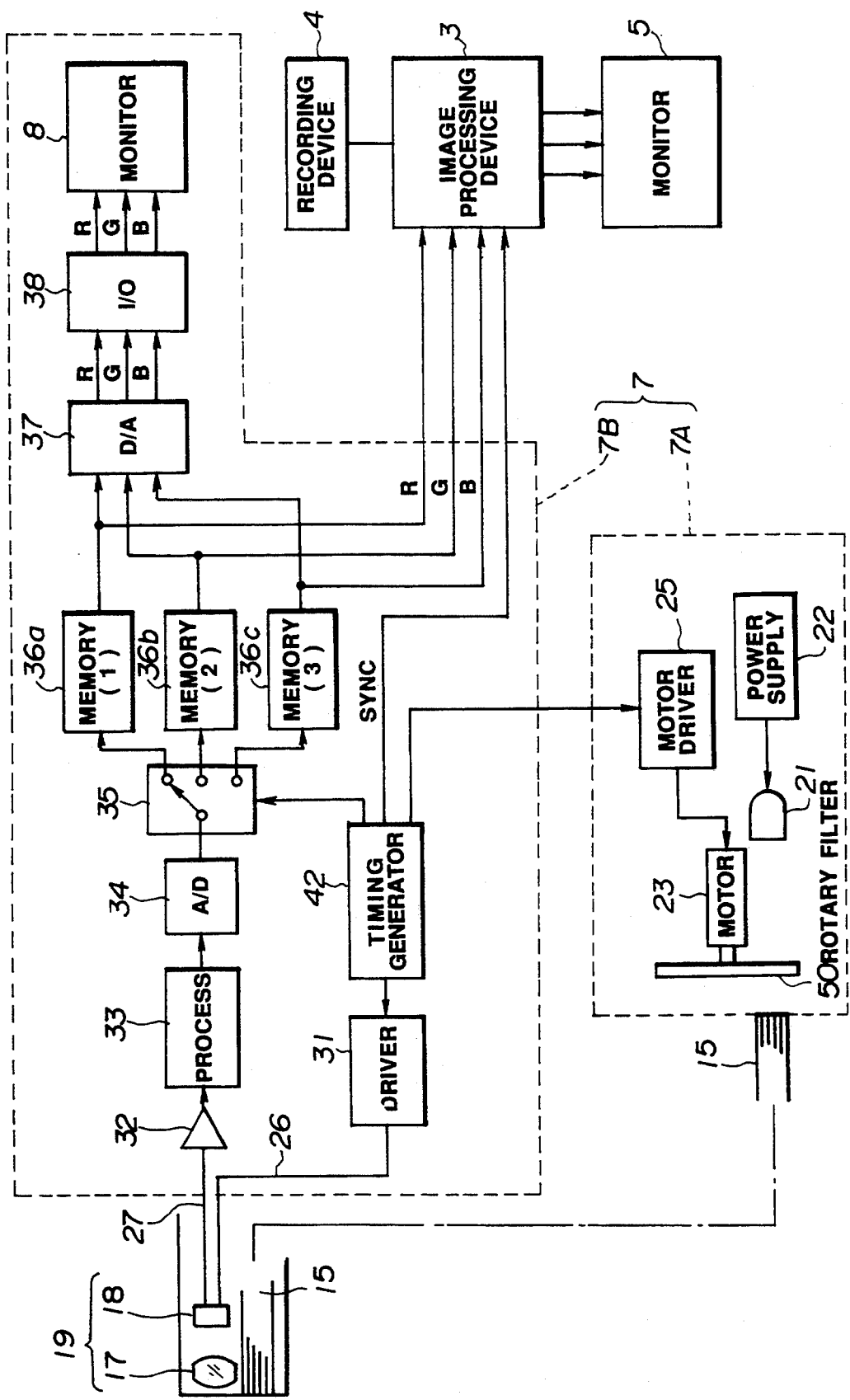

In the insertion portion 11 is inserted a light guide 15. When the connector 14 is connected to the observation device 7, the illuminating light is supplied to the incident end surface from the light source portion 7A, as shown in FIG. 2. The illuminating light is transmitted by the light guide 15 and is forwardly emitted from the end surface on the tip side 16 to illuminate an object part in the living body 9. The image of the object part illuminated is formed on a CCD 18 disposed at an imaging position by an objective lens 17 provided at the tip portion 16, and is subjected to photoelectric conversion. The objective lens 17 and the CCD 18 constitutes an imaging section 19 serving as the imaging means.

The image signal subjected to photoelectric conversion by the CCD 18 is processed by the signal processing section 7B in the observation device 7 to generate an image signal. The image signal is output to the observation monitor 8 and to the image processing device 3.

FIG. 2 illustrates the configuration of the light source portion 7A and the signal processing portion 7B in the observation device 7.

The light source portion 7A is provided with a lamp 21 emitting light within a wide range from ultraviolet light to infrared light. A general xenon lamp, strobolamp or the like can be used as the lamp 21. The xenon lamp and strobolamp emit large quantities of not only visible light but also ultraviolet and infrared light.

The lamp 21 is designed so that electric power is supplied from a power source 22. A rotary filter 50 rotated by a motor 23 is disposed in front of the lamp 21. Filters which respectively transmit usual observation light within the wavelength regions of the red (R), green (G) and blue (B) are disposed on the rotary filter 50 in the peripheral direction thereof.

The motor 23 is driven so that the rotation thereof is controlled by a motor driver 25. The light transmitted through the rotary filter 50 and separated into light portions within the wavelength regions of R, G and B in a time series manner is then applied to the incident end of the light guide 15. The light is then guided to the emission end on the tip side 16 through the light guide 15 and is forwardly emitted from the emission end to illuminate an observation position or the like.

An image of the light returned from a specimen (object) such as an observation position or the like illuminated by the illuminating light is formed on the CCD 18 by the objective lens 17 and is subjected to photoelectric conversion. A driving pulse is applied to the CCD 18 from the driver 31 in the signal processing portion 7B through a signal line 26. The driving pulse causes the read of only electric signals (video signal) corresponding to the specimen image subjected to photoelectric conversion.

The electric signals read from the CCD 18 are input to a preamplifier 32 provided in the electronic endoscope 6 or the observation device 7. The video signals amplified by the preamplifier 32 are input to a processing circuit 33, subjected to signal processing such as g-correction, white balance and the like, and are then converted into digital signals by an A/D converter 34.

The digital video signals are selectively stored by a select circuit 35 in three memory units, i.e., memory (1) 36a, memory (2) 36b, and memory (3) 36c, for example, corresponding to colors of read (R), green (G) and blue (B), respectively. The R, G, B color signals stored in the memory (1) 36a, (2) 36b and (3) 36c are simultaneously read, converted into analog signals by a D/A converter 37, and then output as R, G, B color signals to a color monitor 8 through an input/output interface 38. The color monitor 8 performs a color display of the observation position.

In the observation device 7 is also provided a timing generator 42 for forming timing for the whole system. The timing generator 42 causes synchronism between circuits such as the motor driver 25, the driver 31, the select circuit 35 and so on.

In this embodiment, the output terminals of the memory units (1) 36a, (2) 36b and (3) 36c, and the synchronizing signal output terminal of the timing generator 42 are connected to the image processing device 3. The image processing device 3 is connected to the color monitor 5 so that the operation results obtained from the image processing device 3 are displayed on the color monitor 5.

Figure 3:
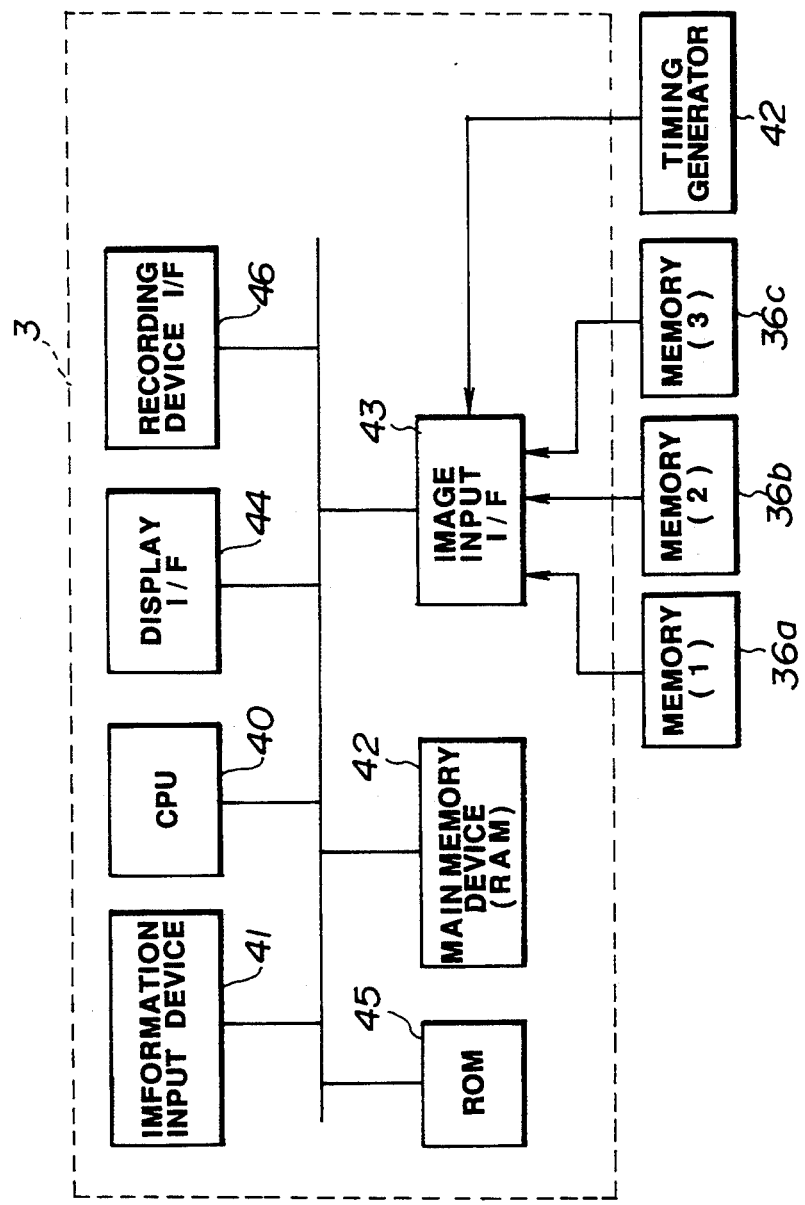

FIG. 3 shows the configuration of the image processing device 3. The image processing device 3 comprises a CPU 40, an information input device 41, a main memory device 42 comprising a RAM, an image input interface 43, a display interface 44, a ROM 45 and a recording device interface 46, all of which are connected to each other through a bus.

Figure 4:
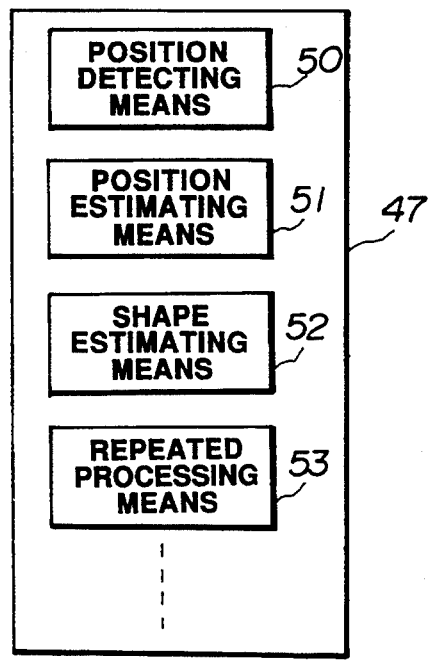

The CPU 40 has image processing means 47 operated by the program stored in the ROM 45, as shown in FIG. 4. The image processing means 47, for example, comprises position detection means 50 for detecting the positions of the same point on a plurality of images of an object formed by the imaging means, position estimating means 51 for estimating the position of the imaging means from the positions of the same point on the images, shape estimating means 52 for estimating a three-dimensional shape of the object from the position of the same point and position of the imaging means, which are estimated by the position estimating means 51, and repeated processing means 53 for detecting the positions of the same point on the object in the images, estimating the position of the imaging means and repeatedly estimating a three-dimensional shape of the object, and so forth.

The information input means 41 comprises a key board or the like so that data such as the type of the electronic endoscope 6 and the like can be input. The image input interface 43 are connected to the memory units (1) 36a, (2) 36b and (3) 36c so as to receive the image data therefrom. The display interface 44 sends the image data input to the monitor 5.

Figure 5:
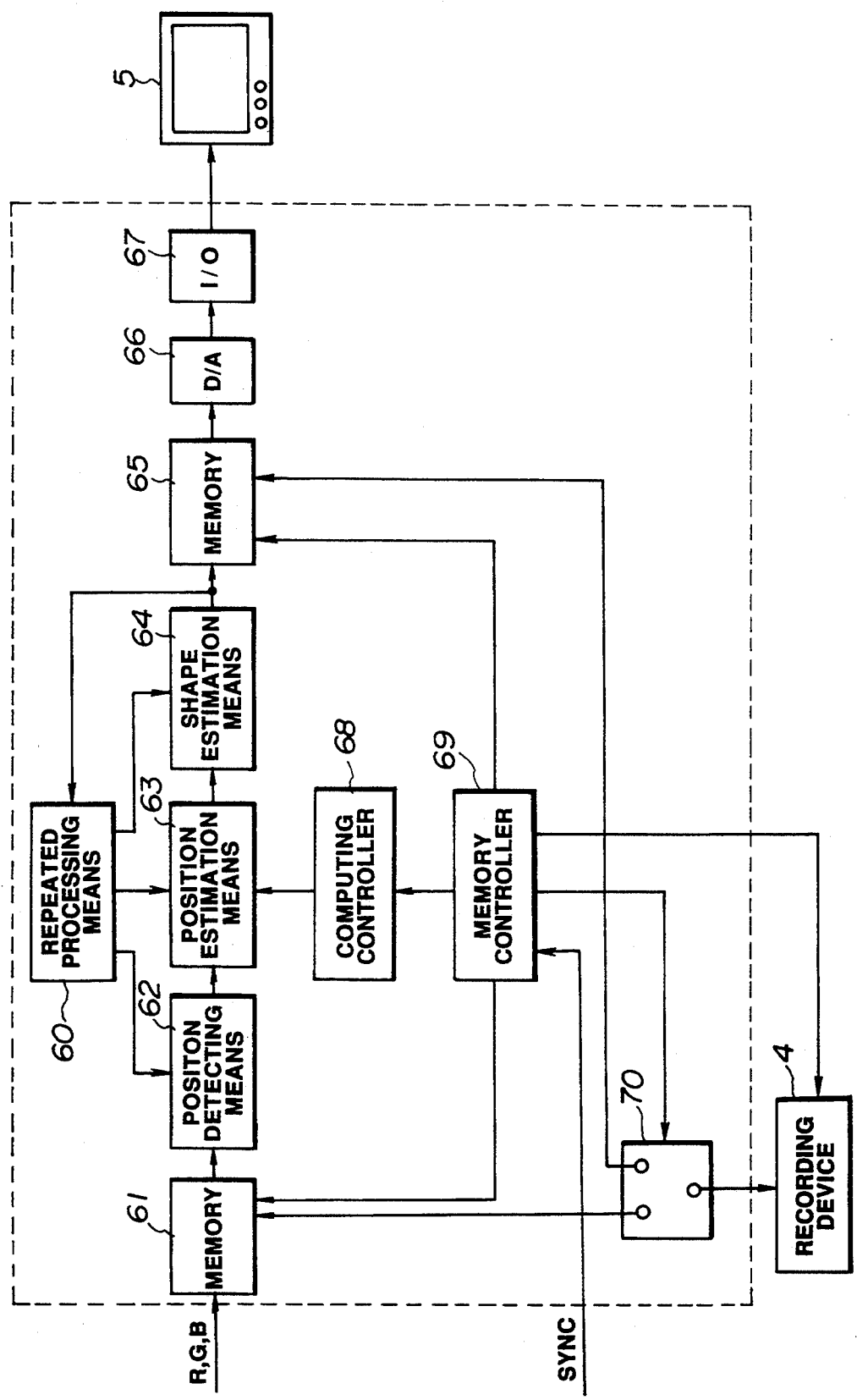

FIG. 5 is a block diagram showing the image processing device 3 comprising hardware for operation.

The time series image data recorded in the memory units (1) 36a, (2) 36b and (3) 36c is once stored in a memory 61. A three-dimensional shape of an object is computed by position detection means 62, position estimating means 63, shape estimating means 64 and repeated processing means 60 on the basis of the image data stored, and three-dimensional image data or two-dimensional image data is stored in memory 65.

The three-dimensional image data or two-dimensional image data stored in the memory 65 is read, converted into analog signals by a D/A converter 66 and is displayed as a three-dimensional or two-dimensional image of the object position on the monitor 5 through an input/output interface 67.

The image processing device 3 is also provided with an operation controller 68 for controlling the operations of the position detecting means 62, the position estimating means 63, the shape estimating means 64 and the repeated processing means 60, and a memory controller 69 for controlling data read and write of the memory units 61 and 65. A selector 70 selectively connects one of the memory units 61 and 65 to a the recording device 4 on the basis of the control signal of the memory controller 69 so that data can be transmitted between the recording device 4 and the memory unit 61 or 65.

In this embodiment, the images of an object position obtained by the electronic endoscope 6 are processed by the image processing device 3, and the processing results are output to the monitor 5.

Figure 6:
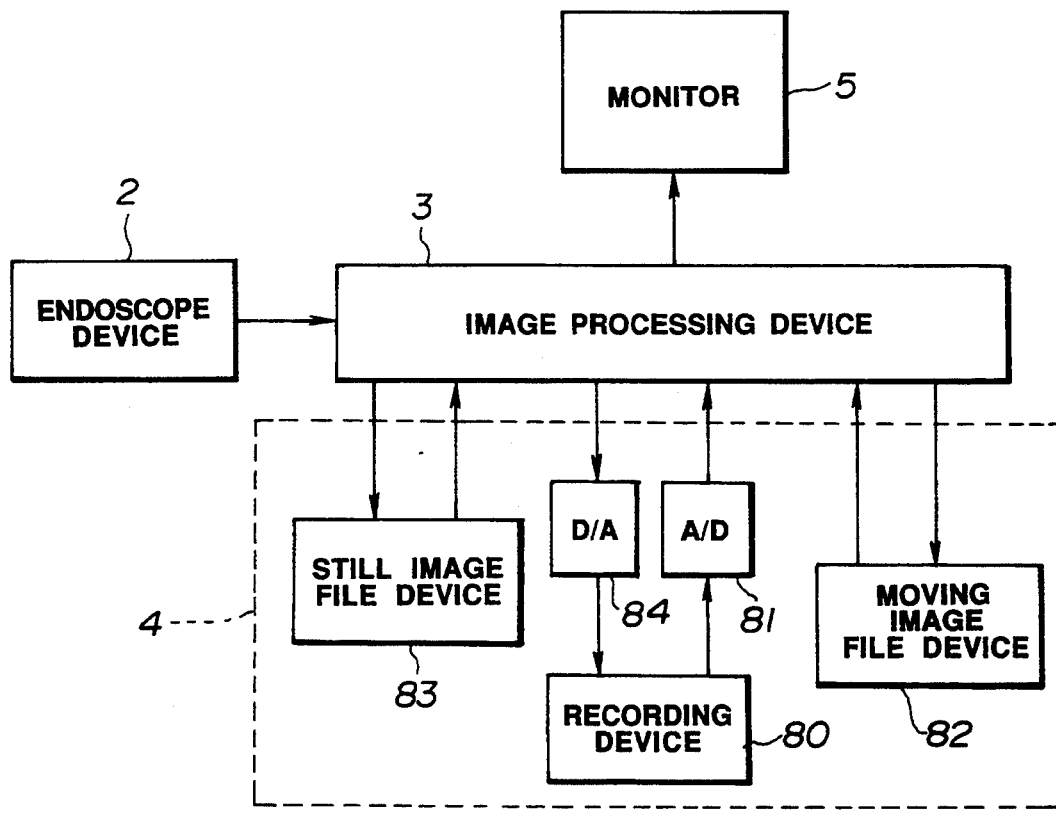

FIG. 6 shows a typical example of the configuration of the recording device 4 connected to the image processing device 3 so as to record image data to be processed by the image processing device 3 and record the image data processed and displayed on the monitor 5.

An image recording device 80 is a VTR or an analog image recording device such as an analog magneto-optic disk device or the like. The output of the recording device 80 is subjected to A/D conversion by an A/D converter 81 and is then input as a digital image to the image processing device 3. The image of the processing results obtained by the image processing device 3 can also be recorded in the image recording device 80 through a D/A converter 84.

A moving image file device 82 is a digital moving image file device comprising semiconductor memory, a hard disk, a digital optical magneto-optic disk or the like. The output of the moving image file device 82 is input as a digital image to the image processing device 3.

A still image file device 83 is a digital still image file device comprising semiconductor memory, a hard disk, a digital magneto-optic disk or the like, like the moving image file device 82. The output of the still image file device 83 is input as a digital image to the image processing device 3.

The image of the processing results obtained from the image processing device 3 can also be recorded in the moving image file device 82 and the still image file device 83.

In FIG. 2, the image signal subjected to photoelectric conversion by the CCD 18 is processed by the signal processing portion 7B in the observation device 7 and is then output to the observation monitor 8 and to the image processing device 3.

The two-dimensional image data input to the image processing device 3 is once sent to the recording device 4 and recorded as an image signal therein. The image signal recorded is again sent to the image processing device 3, processed for estimating a three-dimensional shape of an object therein, and is then sent to the recording device 4 and the monitor 5 so that the estimated three-dimensional shape is recorded and displayed on the recording device 4 and the monitor 5, respectively.

In the first embodiment, processing for determining a three-dimensional image from a two-dimensional image is performed in the accordance with the procedure below.

The image signals of the endoscopic image obtained by the electronic endoscope 6 are successively transmitted to the image processing device 3 by the observation device 7. The image processing device 3 sends the image signals of the endoscopic image successively transmitted for an any desired period to the recording device 4 and records the signals therein.

The image data in a plurality of frames of the endoscopic image data (two-dimensional image data) recorded in the recording device 4 is sent to the image processing device 3. The position of the same point is detected from the image data of the plurality of frames, and shift maps indicating the movement of the detected positions are then formed by computation.

The movement vector (movement vector of the tip of the electronic endoscope 6) of the imaging means is estimated from the shift maps formed. Each of two-dimensional shapes is estimated by using the estimated movement vector of the imaging means and the shift maps of the images. The respective estimated shapes are weighted in accordance with the reliability and added to determine a three-dimensional shape.

Image data indicated by a two-dimensional image or three-dimensional image (wire frame or the like) as viewed from the imaging means in any desired direction thereof is formed for the determined three-dimensional data. The three-dimensional image data or two-dimensional image data formed by the image processing device 3 is simultaneously displayed and recorded on the monitor 5 and in the recording device.

Figure 7A:
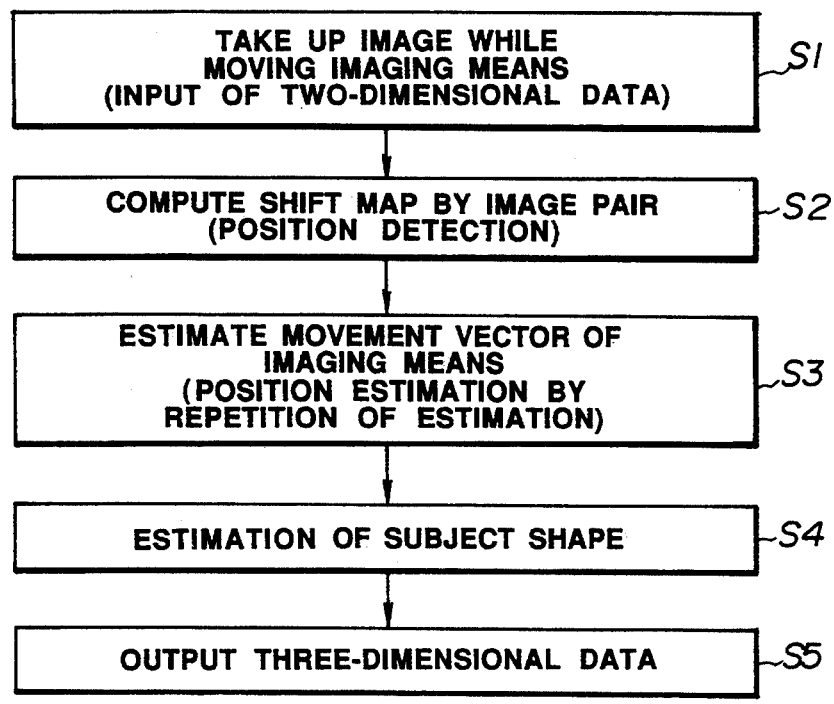
FIGS. 7a and 7b are flowcharts showing processing contents up to the step of converting two-dimensional image data into three-dimensional data by an image processing device.
Figure 7B:
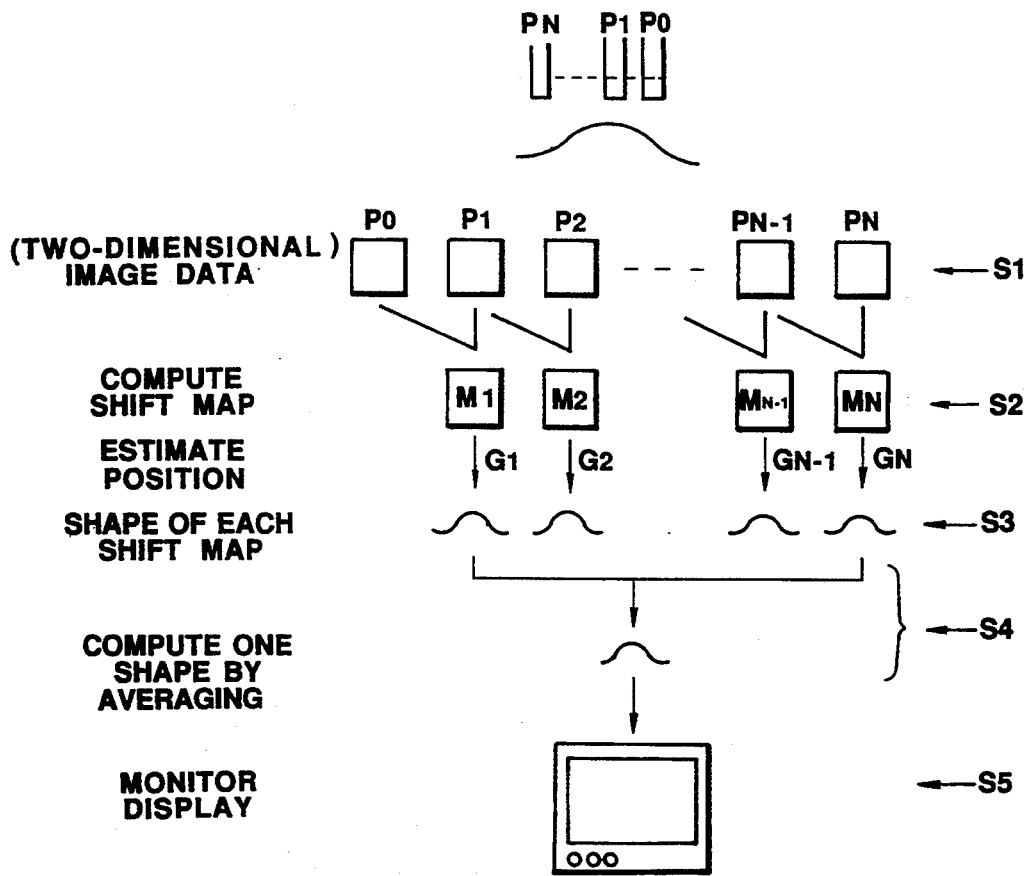

FIGS. 7a and 7b are flow charts showing the process up to the step of converting the two-dimensional image data to the three-dimensional image data by the image processing device 3. The process up to the step of calculating three-dimensional image data is described below.

In Step S1, the images formed by the imaging means moving are input to the image processing device 3. Namely, two-dimensional image data about different positions of the same object are input while the imaging means (the tip of the electronic endoscope 6) is moved little by little.

In Step S2, the distortion of each of the images obtained in Step S1 is then corrected by distortion aberration correction. The distortion aberration correction is complimentarily described below.

Figure 8A:
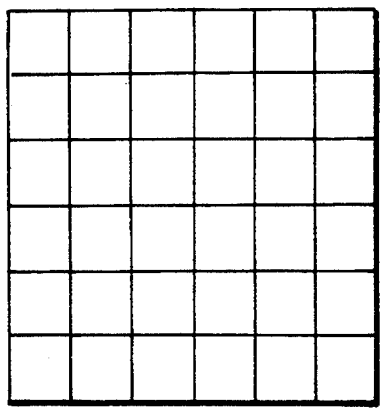
FIGS. 8a and 8b are drawings explaining the correction of distortion aberration.
Figure 8B:
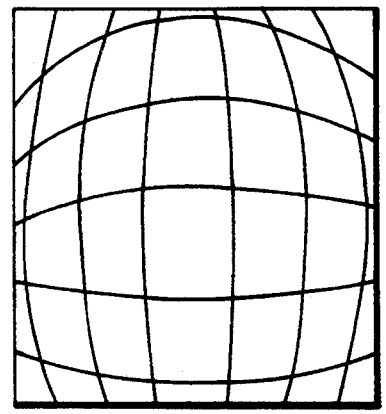

Since the endoscopic image data sent from the recording device 4 has the distortion caused by a wide angle lens, the distortion of each image is corrected by distortion aberration correction. For example, when the square cells shown in FIG. 8a are imaged by the electronic endoscope 6, the image obtained is as shown in FIG. 8b. The correction value for each of the images is previously determined so that the distorted image shown in FIG. 8b becomes a square cell image, whereby distortion aberration correction can be realized by correcting actual images using the correction values. A specific correction processing method is disclosed in U.S. Pat. No. 4,895,431.

Corresponding point tracing is then performed by using a plurality of corrected images (image pair). Namely, an image (template image) showing the object is selected, and a plurality of points on the selected image are selected and traced to the the same points on another reference image. The corresponding point tracing is described below.

Figure 9A:
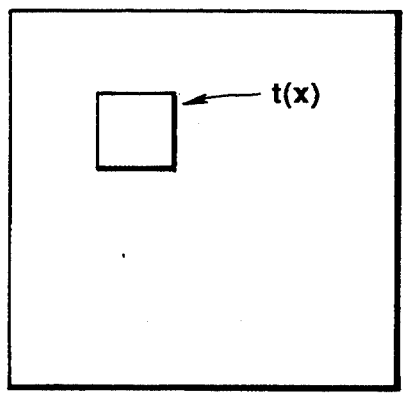
FIGS. 9a and 9b are drawings explaining the step of determining a shift amount between a template image and a reference image.
Figure 9B:
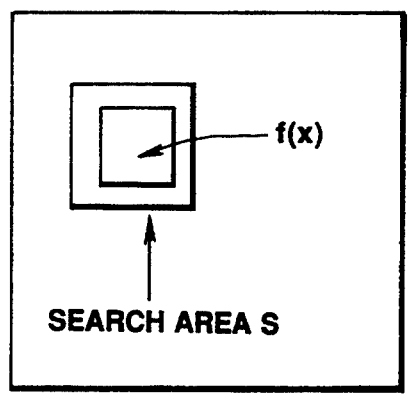

In the corresponding point tracing, a rectangular area (window) having a point on the template image of the detection object at the center thereof is denoted by t(x), as shown in FIG. 9a, and a search area S having a certain size is set on the reference image, as shown in FIG. 9b. Processing for block matching between the rectangular area t(x) in the template image and a corresponding area f(x) in the search area is performed by correlation operation for determining an area having a maximum correlation value. The direction and amount of the movement of the selected points in the reference image to the template image are determined.

For example, a correlation value is determined using the following normalized correlation D(u, v):

$$D(u,v) = \frac{\int\int s[\{f(x+u, y+v) - <f>\}\{t(x,y) - <t>\}]dxdy}{\sqrt{[\int\int s \{f(x+u, y+v) - <f>\}^2 dxdy \int\int \{t(x,y) - <t>\}^2 dxdy]}}$$

An area with the maximum correlation value is determined, and the direction and amount of the movement of the area are then determined. In the correlation D(u,v), $\int\int$ s indicates integration in the search area S, and $<f>$ and $<t>$ indicate the averages of f(x+u, y+v) and t(x, y), respectively, within the search area S.

The block matching processing is not limited to correlation operation, and the color matching disclosed in U.S. Pat. No. 4,962,540 by the same applicant as that of this invention (refer to the "Introduction to Computer Image Processing" edited by Hideyuki Tamura, Soken Shupan K. K., P. 148-150).

A shift map showing the direction and amount of the movement of the selected point on the template image is determined as described above.

In Step S3, the kinetic vector of the imaging means is determined by repeated processing such as the method of steepest descent or the like using the shift map determined in Step S2 to determine the relative positional relation between the object and the imaging means.

The positional relations between the object and the imaging means, which are determined by the respective shift maps, are transformed into the same coordinate space, and the positional relations between the same points on the object and the imaging means are averaged to determine the shape of the object. The estimated three-dimensional image data is then output to the display device side or the like in Step S6.

The steps of computing the three-dimensional image data are successively described below.

(I) Formation of Shift Map from Input Image (Position Detection)

Images of an object position in the living body 9 or the like to be internally examined are formed by the endoscopic device 2, and are recorded in the recording device 4.

In this case, a plurality of images of same position of the object, which are formed by moving the tip of the electronic endoscope 6 little by little, are recorded in the recording device 4. As a result, endoscopic image data comprising a string of images f0 to fm (shown at the right of FIG. 10) formed by moving the tip 16 (imaging means contained therein) of the electronic endoscope 6 shown at the left of FIG. 1 are obtained.

The image processing device 3 performs distortion aberration correction for the endoscopic image data sent from the recording device 4. The corrected endoscopic image data (two-dimensional image data) of m+1 frames (image string f0 to fm) is divided into N groups. Corresponding point tracing corresponding to the movement locus of the imaging means is then performed for the image groups P0 through PN each having i+1 frames of image data to form a shift map for each group.

Figure 10:
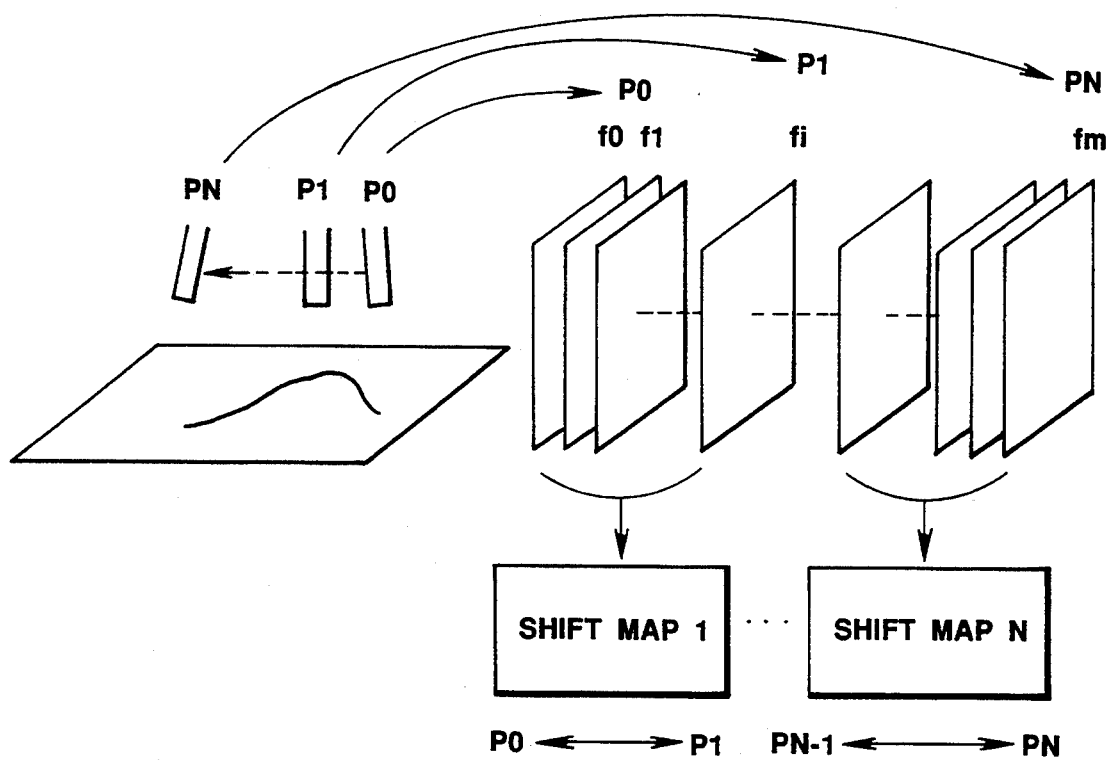

The shift map 1 shown in FIG. 10 is formed by successively calculating the amounts of movement between the respectively frames using the image data comprising the i+1 image frames f0 to fi in a string while performing corresponding point tracing by the following two methods:

(1) A correspondence between the image data f0 and f1 is first determined, and correspondences between the image data f1 and f2, and f2 and f3 are then determined in this order. All items of data on the movement amounts are added to determine a correspondence between the image data f0 and fi.

(2) A correspondence between the image data f0 and f1 is determined, and a correspondence between the image data f0 and f2 is then determined on the basis of the data on the movement amount obtained. A correspondence between the image data f0 and f3 is then determined on the basis of the data obtained from the correspondence between the image data f0 and f2. A correspondence between the image data f0 and fi is finally determined.

At a time during corresponding point tracing performed by each of the methods (1) and (2), an increase in parallax of the image data f0 and fk+1 from the image data f0 and fk in the method (2) is compared with a parallax between the image data fk and fk+1. When the difference in parallax between the method (1) and (2) exceeds a predetermined value (3 pixels on the experimental base), it is decided that mismatching occurs, and the movement amount of the corresponding point is estimated again from the data of the peripheral portion using an interpolation function. The processing contents are shown by the flow chart of FIG. 11.

The image data fm is taken up in Step S11, and distortion aberration correction processing is then performed in Step S12. The data of (m+1) images fm+1 is divided into N groups in next Step S13. In subsequent steps from S14, each of the image areas divided into the N groups is subjected to corresponding point tracing by each of the methods (1) and (2), and a decision is made as to whether or not a variation in parallax exceeds a threshold.

Namely, n is first set to zero in Step S14, corresponding point tracing is performed between image data fm (image data fm+1) and the image area of n=0 by the methods (1) and (2) in next Steps 15a and 15b, respectively. A variation in parallax between the results of the methods (1) and (2) is calculated in Step S16.

A decision is made in Step S17 as to whether or not the variation in parallax exceeds a threshold (the above constant value). If the variation exceeds the threshold, interpolation processing is made in Step S18. If the variation is smaller than the threshold, a decision is made in Step S19 as to whether or not n=N. If n is not N, n is set to (n+1) in Step S20, and the flow returns to Steps 15a and 15b in which the same processing as that described above is performed for the next image area. In this way, the same processing is performed for all the divided image areas to n=N.

Figure 11:
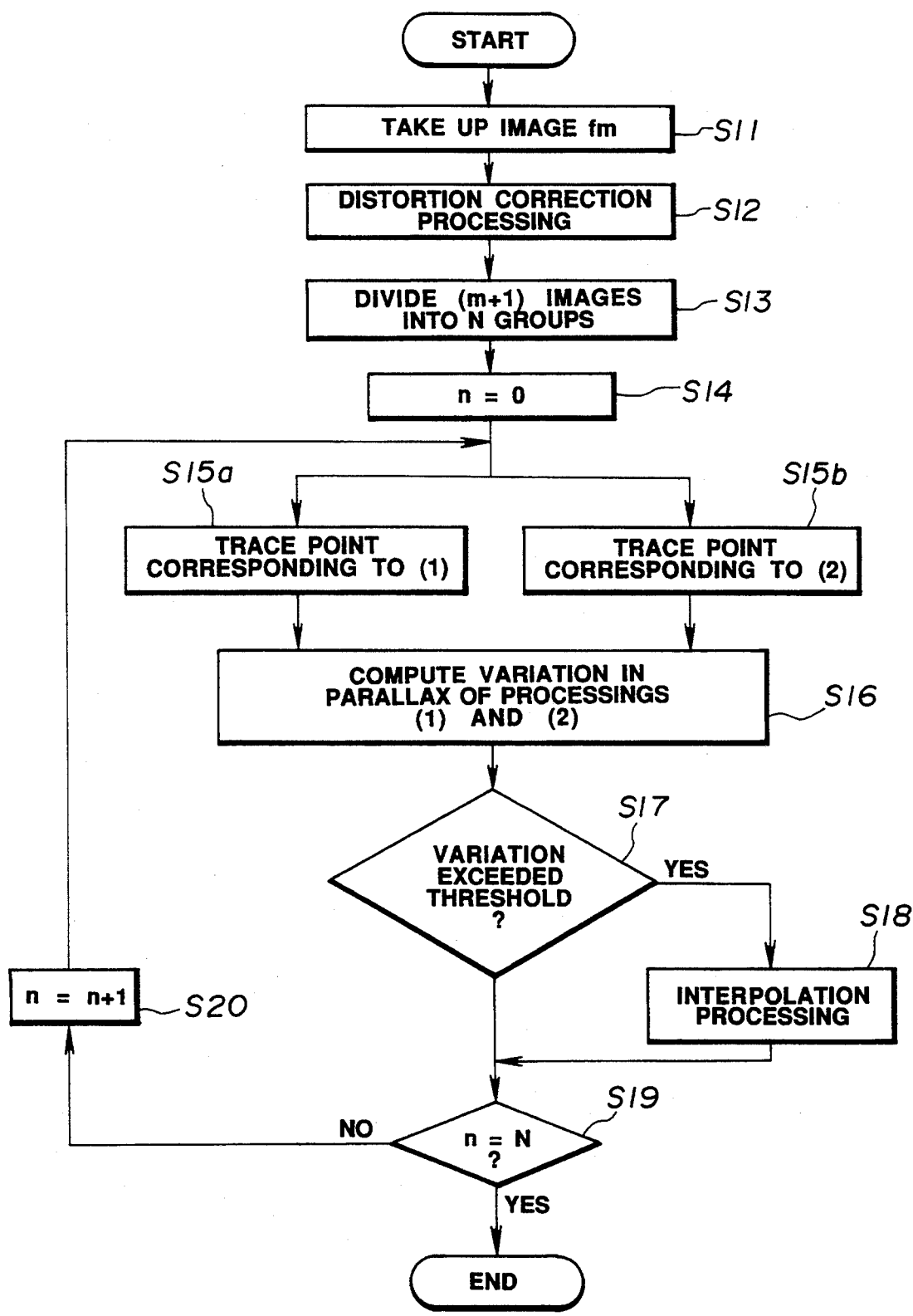

The shift amounts between the respective corresponding points of the respective images are determined in accordance with the processing shown in FIG. 11, and the shift amount between the image data f0 and fi, i.e, P0 and P1, is finally determined to form the shift map 1.

In the same way, shift maps 2 to N (shift amount between PN−1 and PN) are determined. The computation of the N shift maps causes the movement amounts of the corresponding points on the images P0 to PN formed by the imaging means to be computed with connection between the respective images. If a position on an image is determined, the position of the same point on each of other images can thus be computed.

(II) Prediction of Position by Predicting Movement

The movement of the imaging means (movement of the tip 16 of the endoscope) is estimated from the determined shift maps using 8-point algorithm. However, if the correspondence between the respective images includes error, a correct solution cannot be obtained by the 8-point algorithm. The method of least squares is thus introduced into the 8-point algorithm, and a solution is obtained by using the method of steepest descent to determine the movement vector of each of the shift maps.

The 8-point algorithm is described below (refer to "Image Understanding" edited by Kenichi Kanaya, Shinhoku Shupan K. K.).

Figure 12:
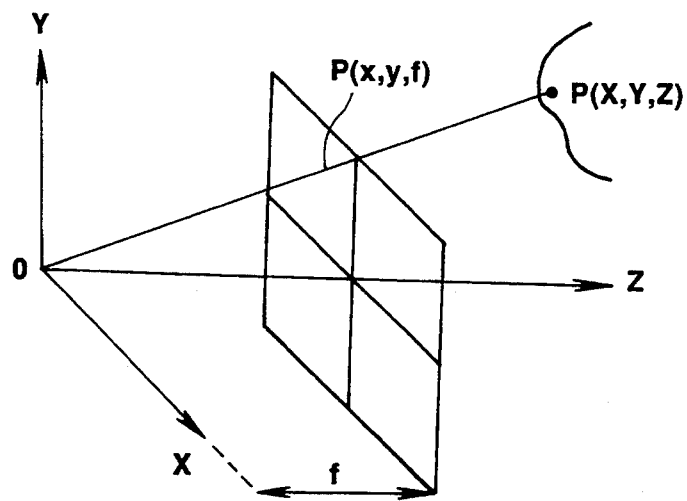

FIG. 12 shows a coordinate system of central projection. In FIG. 12, an image plane is vertically placed on the Z axis at a distance f from the image origin O. In this case, it is assumed that a point (X, Y, Z) in a space is projected on the intersection of the image plane and a line connecting the point (X, Y, Z) and the origin O. Assuming that the image coordinates of the point (X, Y, Z) are (x, y), x and y are expressed by the following equations using the geometric relation:

$$x = Xf/Z \quad y = Yf/Z \tag{1}$$

Figure 13:
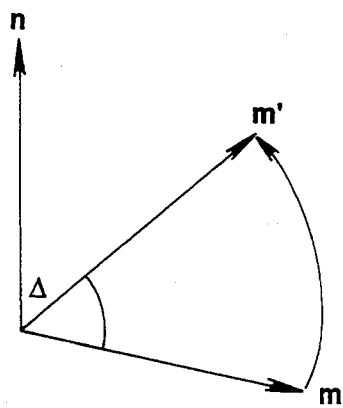

When a point X (X, Y, Z) is moved to a point X' (X', Y', Z') by the movement of the imaging means, the movement of the imaging means is shown by the following equation using the orthogonal matrix R indicating the rotation around the visual line passing through the origin and the translational vector h=(hx, hy, hz):

$$X = RX' + h \tag{2}$$

wherein assuming that n=(nx, ny, nz) is the direction of the rotation axis, and that q is the angle of rotation, as shown in FIG. 13, R is expressed as follows:

$$R = \begin{pmatrix} nx^2 + (1 - nx^2)\cos\theta & nxny(1 - \cos\theta) - nz\sin\theta & nxnz(1 - \cos\theta) + ny\sin\theta \\ nxny(1 - \cos\theta) + nz\sin\theta & ny^2 + (1 - ny^2)\cos\theta & nynz(1 - \cos\theta) - nx\sin\theta \\ nxnz(1 - \cos\theta) - ny\sin\theta & nynz(1 - \cos\theta) + nx\sin\theta & nz^2 + (1 - nz^2)\cos\theta \end{pmatrix} \tag{3}$$

The points X and X' are expressed by the following equations using the distances from the origin and the unit direction vectors m (N vectors) and m', respectively:

$$X = \begin{pmatrix} X \\ Y \\ Z \end{pmatrix} = rm \quad X' = \begin{pmatrix} X' \\ Y' \\ Z' \end{pmatrix} = r'm' \tag{4}$$

$$m = \frac{1}{\sqrt{(x^2 + y^2 + z^2)}} \begin{pmatrix} x \\ y \\ f \end{pmatrix}$$

$$m' = \frac{1}{\sqrt{(x'^2 + y'^2 + z'^2)}} \begin{pmatrix} x' \\ y' \\ f \end{pmatrix} \tag{5}$$

In addition, the equation (2) is shown by the equation (5) as follows:

$$rm = r'Rm' + h \tag{6}$$

Figure 14:
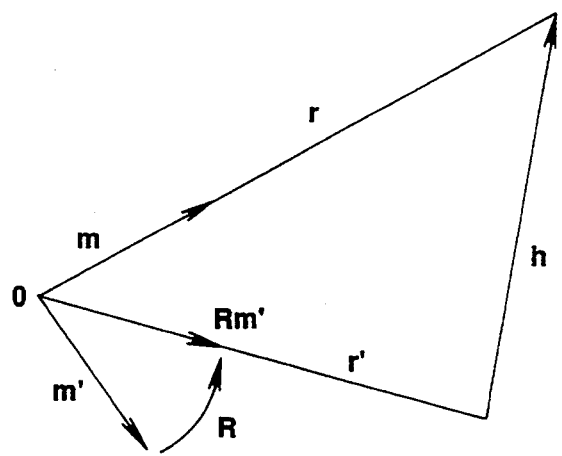

Since the three vectors m, Rm' and h are present on the same plane in a space, as shown in FIG. 14, the scalar triple product of the vectors is zero. This is expressed by the following equation:

$$|mhRm'| = (m, h \times Rm') = 0 \tag{7}$$

In the equation (7), if the outer product of h and R is G, the following equation is established:

$$(m, Gm') = 0 \tag{8}$$

wherein $$G = (h \times r1, h \times r2, h \times r3) \tag{9}$$

and r1, r2 and r3 are the first, second and third column vectors, respectively, of R. The vector products of the both sides of the equation (6) and h are expressed by the following equation:

$$rh \times m = r'h \times Rm'(=r'Gm) \tag{10}$$

The inner products of the both sides of the equation (10) and h×m are as follows:

$$r \| h \times m \|2 = r'(h \times m, Gm')(=r'|hmGm'|) \tag{11}$$

As a result, the following equation is obtained:

$$|hmGm'| \geq 0 \tag{12}$$

The elements of G are determined from R and h. The equation (8) is a simultaneous equation related to the 9 elements of G. The ratio of the elements of G can thus be determined by the eight equations of the first degree obtained from the eight corresponding pairs.

The result obtained by multiplying G by a constant so that:

$$T\{GG^T\} = 2 \tag{13}$$

is shown by $\hat{G}$. This corresponds to normalization of the translation vector h to the unit vector.

According to the equations (8) and (9), the translation vector h intersects at right angles all column vectors of G. Assuming that the column vectors of $\hat{G}$ are $g\hat{\ }1$, $g\hat{\ }2$ and $g\hat{\ }3$, the unit vector h is calculated by the following equation:

$$(\hat{g}\hat{h}) = 0, \; i = 1, 2, 3 \quad (14)$$

The sing is determined by the equation (12) so that the following equation is established:

$$|\hat{h}^{\wedge}m\alpha G\hat{\ }m'\alpha| \geqq 0, \; \alpha = 1, \ldots, 8 \quad (15)$$

The unit vectors (r^1, r^2, r^3) which intersect each other at right angles to form the right-hand system so the the equation (16) below is established are then determined on the basis of the equation (9).

$$\hat{h} \times \hat{r} = \hat{g}i, \; i = 1, 2, 3 \quad (16)$$

The matrix having the unit vectors as columns in this order is expressed by R = (r 1, r 2, r 3).

The inner products of the both sides of the equation (6) and m and Rm' are respectively expressed by the following equations:

$$\hat{r}\alpha = \hat{r}\alpha(m\alpha, \hat{R}m'\alpha) + (\hat{h}\,\hat{}, \hat{R}\,m'\alpha)$$

$$\hat{r}\alpha(m\alpha, \hat{R}m'\alpha) = \hat{r}\alpha + (\hat{h}\,\hat{}, \hat{R}\,m'\alpha) \quad (17)$$

The distances to each of the points can be determined by solving the equation (17) as shown by the following equations:

$$\hat{r}\alpha = \{(h, m') - (m\alpha, \hat{R}m'\alpha)(\hat{h}\,\hat{}, \hat{R}m'\alpha)\}/\{1 - (m\alpha, \hat{R}m'\alpha)^2\}$$

$$\hat{r}'\alpha = \{(m\alpha, \hat{R}m'\alpha)(\hat{h}\,\hat{}, m\alpha) - (\hat{h}\,\hat{}, \hat{R}m'\alpha)\}/\{1 - (m\alpha, \hat{R}m'\alpha)^2\} \quad (18)$$

As described above, a correct solution cannot be obtained by the 8-point algorithm when error is included in correspondences between the respective images. It is thus necessary to made optimization so that necessary conditions are strictly satisfied, and that other conditions are satisfied on an average.

Assuming that N pairs (N>8) of corresponding points are observed, the matrix G expressed by the following formula is determined by using the method of least squares:

$$\sum_{\alpha=1}^{N} (m\alpha, Gm'\alpha)^2 \to \min, Tr[GG^T] = 2 \quad (19)$$

$$\alpha = 1$$

The matrix G is approximately resolved into the unit vector h and the orthogonal matrix R (least squares algorithm).

The movement parameters h0, R0 of the imaging means are thus estimated by applying restriction conditions to the movement of the imaging means. The unit vector h and the matrix R which minimize the equation (19) are estimated by using the parameters h0 and R0 as initial values. This permits the space where the solution is present to be previously limited, thereby minimizing estimation error.

Figure 15A:
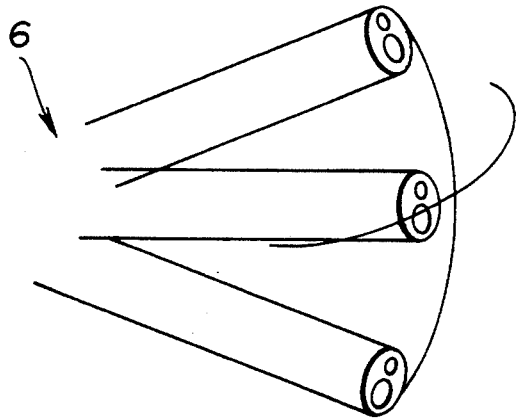
FIGS. 15a and 15b are drawings explaining the movement of the tip of an endoscope.

The initial values of the motion parameters h0 and R0 of the imaging means are determined. As shown in FIG. 15a, the movement of the tip of the electronic endoscope 6 (containing the imaging means moved by external operation) can be considered as a movement in a direction.

Figure 15B:
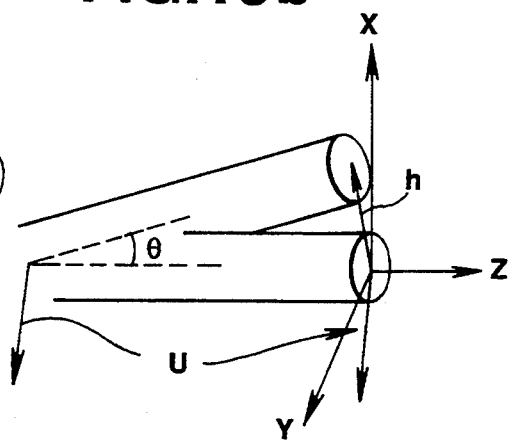

Assuming that the movement of the imaging means in the visual line direction (Z-direction), which is caused by the oscillating motion, is small, that the translation vector indicating the movement is in a plane vertical to the Z axis, that the rotation axis U is vertical to the vector h, and that the angle of rotation q is positive + in the direction of the vector h, as shown in FIG. 15b, the initial values can be determined.

The translation vector h0 is determined by determining the directions of movement of a plurality or points from the shift maps and averaging the directions. When the rotation axis U0 is determined so as to be vertical to the vector h0, three equations including three unknowns r, r' and $\theta$0 can be obtained from the equation (8). The $\theta$0 value can be obtained by solving the three equations.

The values $\theta$0 are determined for a plurality of points, and averaged to obtain the initial value. The optimum solution is obtained form the equation (19) by the method of steepest descent using the initial value obtained.

Figure 16:
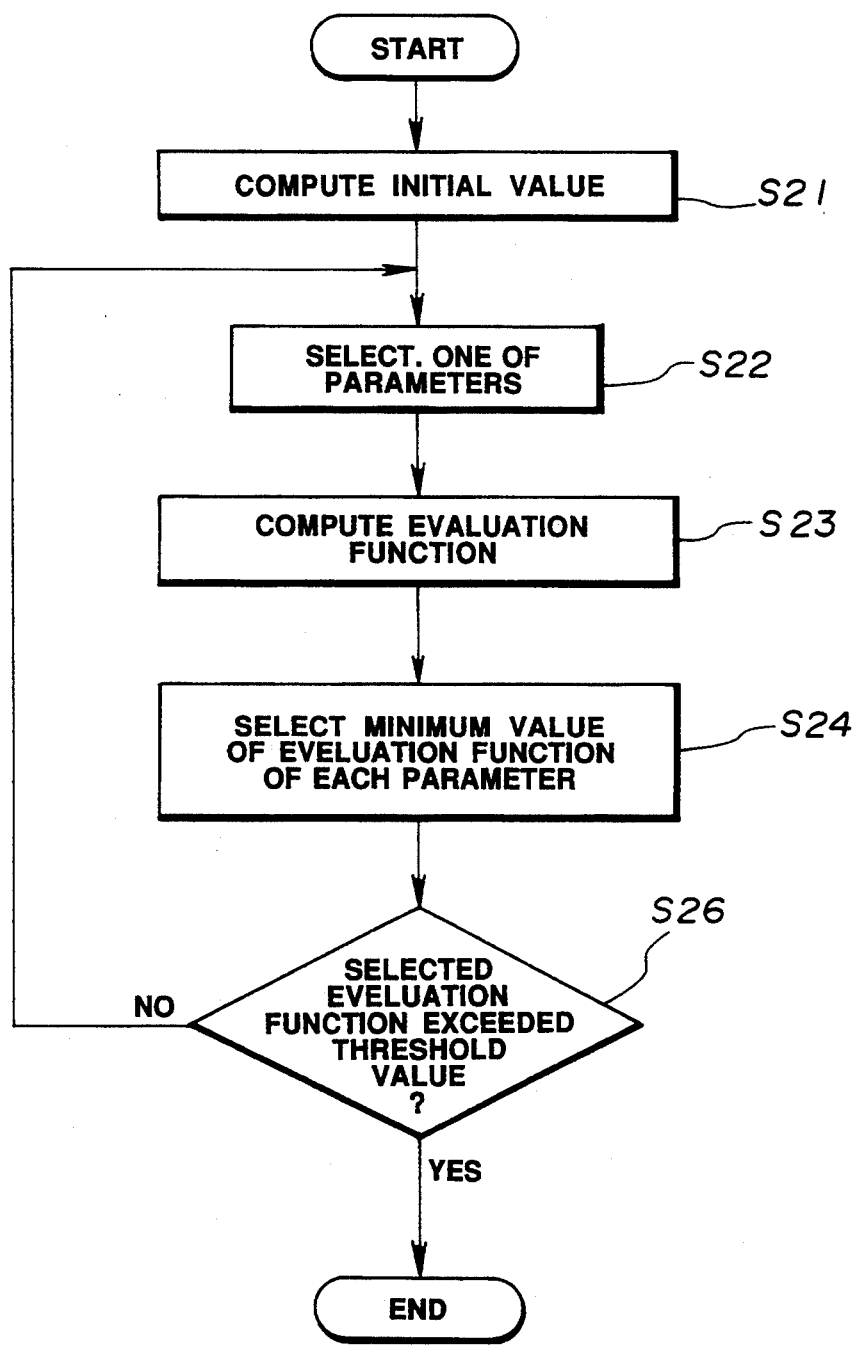

The solution is obtained by the method of steepest descent, as shown in FIG. 16. The elements of the translation vector h and the rotation matrix R of the shift map M(j) in a plurality of shift maps are expressed as follows:

[hx(i), hy(i), hz(i), nx(i), ny(i), nz(i), $\theta$(i)]$_j$ i = 0, 1, 2, . . . , n In Step S21, the translation vector h0 and the rotation matrix R0, which are the initial values of the motion vector, are determined by the method described above with reference to FIGS. 15(a) and 15(b). At this time, each of the initial values is expressed as follows:

hx(0), hy(0), hz(0), nx(0), ny(0), nz(0), $\theta$(0)]$_j$

A parameter of each of the vectors determined is selected in Step S22, and Ad ($\theta$0) is given to the parameter to obtain 14 groups of parameters in all.

[hx(0) + $\Delta d$, hy(0), hz(0), nx(0), ny(0), nz(0), $\theta$(0)]$_j$
[hx(0) − $\Delta d$, hy(0), hz(0), nx(0), ny(0), nz(0), $\theta$(0)]$_j$
[hx(0), hy(0) + $\Delta d$, hz(0), nx(0), ny(0), nz(0), $\theta$(0)]$_j$
[hx(0), hy(0) − $\Delta d$, hz(0), nx(0), ny(0), nz(0), $\theta$(0)]$_j$

.
.
.

[hx(0), hy(0), hz(0), nx(0), ny(0), nz(0), $\theta$(0) + $\Delta d$]$_j$
[hx(0), hy(0), hz(0), nx(0), ny(0), nz(0), $\theta$(0) − $\Delta d$]$_j$ The value of the evaluation function O(i, j) below is determined for each of the parameter groups (Step S23).

$$O(i,j) = \sum_{x=0}^{M} \sum_{y=0}^{N} [(m(x,y), Gm'(x,y)]^2 \quad (20)$$

$$x = 0 \; y = 0$$
$$i = 0, 1, 2, \ldots, 13$$

As described above with respect to the 8-point algorithm, if the G value is correct, the value of (m, Gm') is substantially zero (not zero because m and m' include error). A parameter group showing the minimum value of the 14 evaluation functions O(i, j) determined is thus selected (Step S24). A decision is made in Step S25 as to whether or not the minimum value exceeds a threshold. If it is decided that the minimum value is smaller than the threshold, the flow returns to Step S22 in which the parameter group is renewed. For example, when the first parameter group shows the minimum evaluation function, a new parameter value is determined as follows:

hx(1)=hx(0)+Δd, hy(1)=hy(0), hz(1)=hz(0),
nx(1)=nx(0), ny(1)=ny(0), nz(1)=nz(0),
$\theta(1)=\theta(0)$ In the same way as that described above, Δd ($\geq 0$) is given to the parameter showing the minimum evaluation function as follows:

$[hx(1) + \Delta d, hy(1), hz(1), nx(1), ny(1), nz(1), \theta(1)]_j$
$[hx(1) - \Delta d, hy(0), hz(1), nx(1), ny(1), nz(1), \theta(1)]_j$
$[hx(1), hy(1) + \Delta d, hz(1), nx(1), ny(1), nz(1), \theta(1)]_j$
$[hx(1), hy(1) - \Delta d, hz(1), nx(1), ny(1), nz(1), \theta(1)]_j$ $\vdots$ $[hx(1), hy(1), hz(1), nx(1), ny(1), nz(1), \theta(1) + \Delta d]_j$
$[hx(1), hy(1), hz(1), nx(1), ny(1), nz(1), \theta(1) - \Delta d]_j$ The evaluation function value is determined for each of the parameter groups, and a parameter group showing the minimum evaluation function is selected. The above procedure is repeated to determine the elements of the translation vector h and the rotation matrix R, which minimize the evaluation function O(i, j).

Namely, the movement vector (the translation vector h and the rotation matrix R) can be estimated from one shift map.

The relative positional relation between the visual point and the object at each of the selected points in the respective shift maps can be computed from each of the shift maps and the parameters of the corresponding movement vector by using the equation (18).

(III) Prediction of Shape

The relative positional relations between the object and the imaging means in the respective shift maps can be transformed into the same coordinate space in which a predetermined position of the imaging means is at the origin, and the visual direction is on the Z axis, by the plural motion vectors of the imaging means and the relative positional relations between the object and the imaging means at the selected points in the respective shift maps. Since each of the shift maps and the motion vectors includes error, the relative positional relations between the imaging means and the object are different.

The relative positional relations between the imaging means and the object at each of the same points, which are transformed into the same space, are simply averaged to obtain a value as an estimated shape.

Two-dimensional image data or three-dimensional image data (wire fame or the like) in any desired direction of the imaging means is computed from the three-dimensional data determined by the above procedure and is displayed on the monitor. The three-dimensional data and the computed image data are also recorded in the recording device 4.

In the first embodiment, the positions of the same point on the plural images obtained by moving the imaging means side relative to the object are detected for estimating the relative positional relations between the imaging means and the object from the detected information about the same point, and the shape of the object is estimated from the estimated positional relations.

Namely, the same point on the images formed is detected (determined), and the relative positional relations between the imaging means and the object are estimated on the basis of the information about the same point. The embodiment has the advantage in that even if the object moves with the movement of the imaging means, the relative positional relation between the object and the imaging means can thus be determined with substantially no influence of the movement of the object.

In addition, since the shape of the object is estimated by using the information of the images formed, an additional measuring mechanism such as means for projecting a pattern or the like need not be provided on the electronic endoscope which forms the imaging means, thereby permitting the use of a usual electronic endoscope without increasing the size of the tip portion thereof.

In other words, a usual electronic endoscope with a tip portion which is not increased in size can be used, and when measurement is required, the image processing device 3 is provided on the observation device so that the object can be displayed. It is thus possible to construct a system with excellent extendability.

When the image processing device is applied to medical endoscopy, since a target portion such as an affected part can be displayed in a three-dimensional manner, the degree of swelling at the affected part can be recognized more accurately than conventional endoscopy, thereby causing effective diagnosis.

Further, since the shape of the object is repeatedly estimated by the 8-point algorithm using the motion vectors of the imaging means, the shape can be estimated with high precision.

A second embodiment is described below.

When an actural three-dimensional shape is estimated, an area which cannot be seen from a specified visual point is possibly present in the surface of an object. In the first embodiment, since a three-dimensional shape is estimated by simply averaging the estimated shapes, a large error is possibly included in the estimated three-dimensional shape.

In the second embodiment, a weight function determined by the relation between each visual point and the three-dimensional shape estimated in the first embodiment is introduced for estimating a three-dimensional shape again by repeated processing.

Figure 17:
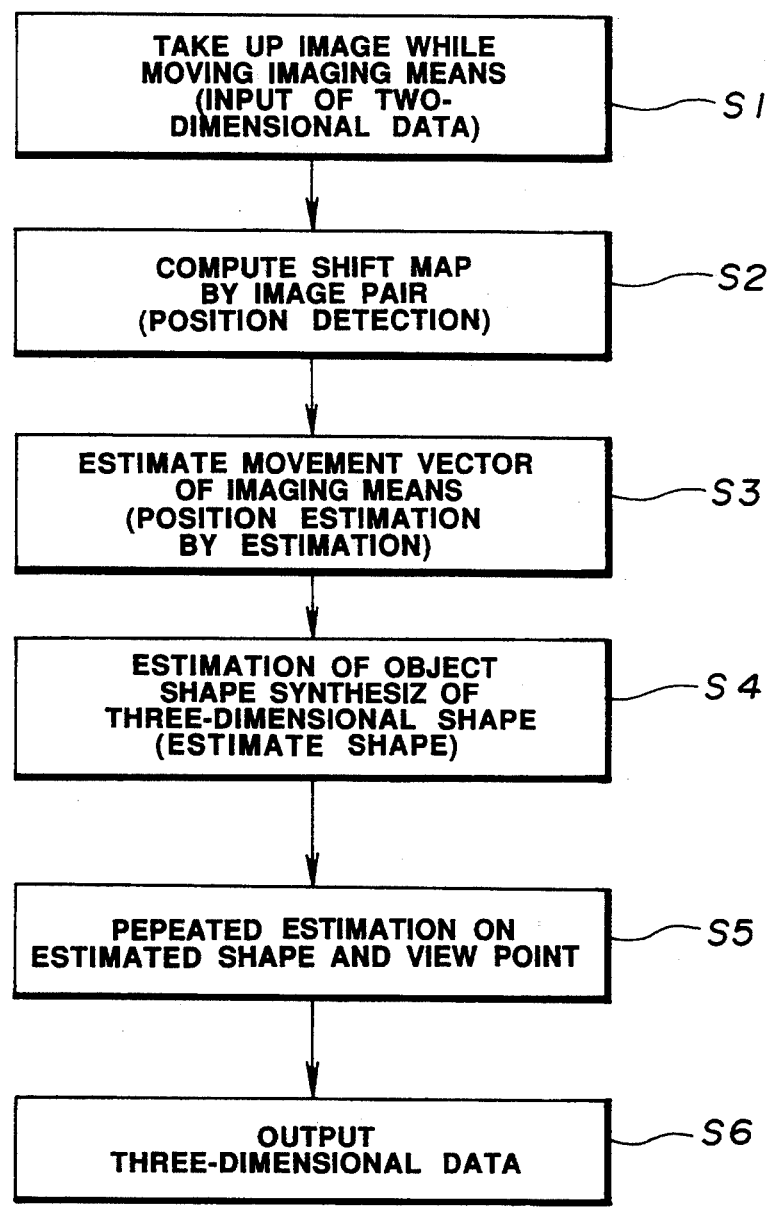
FIG. 17 is a flowchart showing processing contents up to the Step of converting two-dimensional image data into three-dimensional image data in accordance with a second embodiment of the present invention.

FIG. 17 is a flow chart showing the process up to the step of converting two-dimensional image data to three-dimensional image data by the image processing device 3. In FIG. 17, Steps S1 through S4 are the same as those in the first embodiment, a shape is repeatedly estimated in Step S5 on the basis of the three-dimensional shape determined in Step S4. The estimated three-dimensional image data is then output to a display device in Step S6.

A shape is composed by the method employed in the first embodiment using the three-dimensional shapes determined from the respective shift maps, and a three-dimensional shape with higher precision is computed by repeated estimation using the composed shape as an initial value. The calculation method of the repeated estimation is described below.

Figure 18:
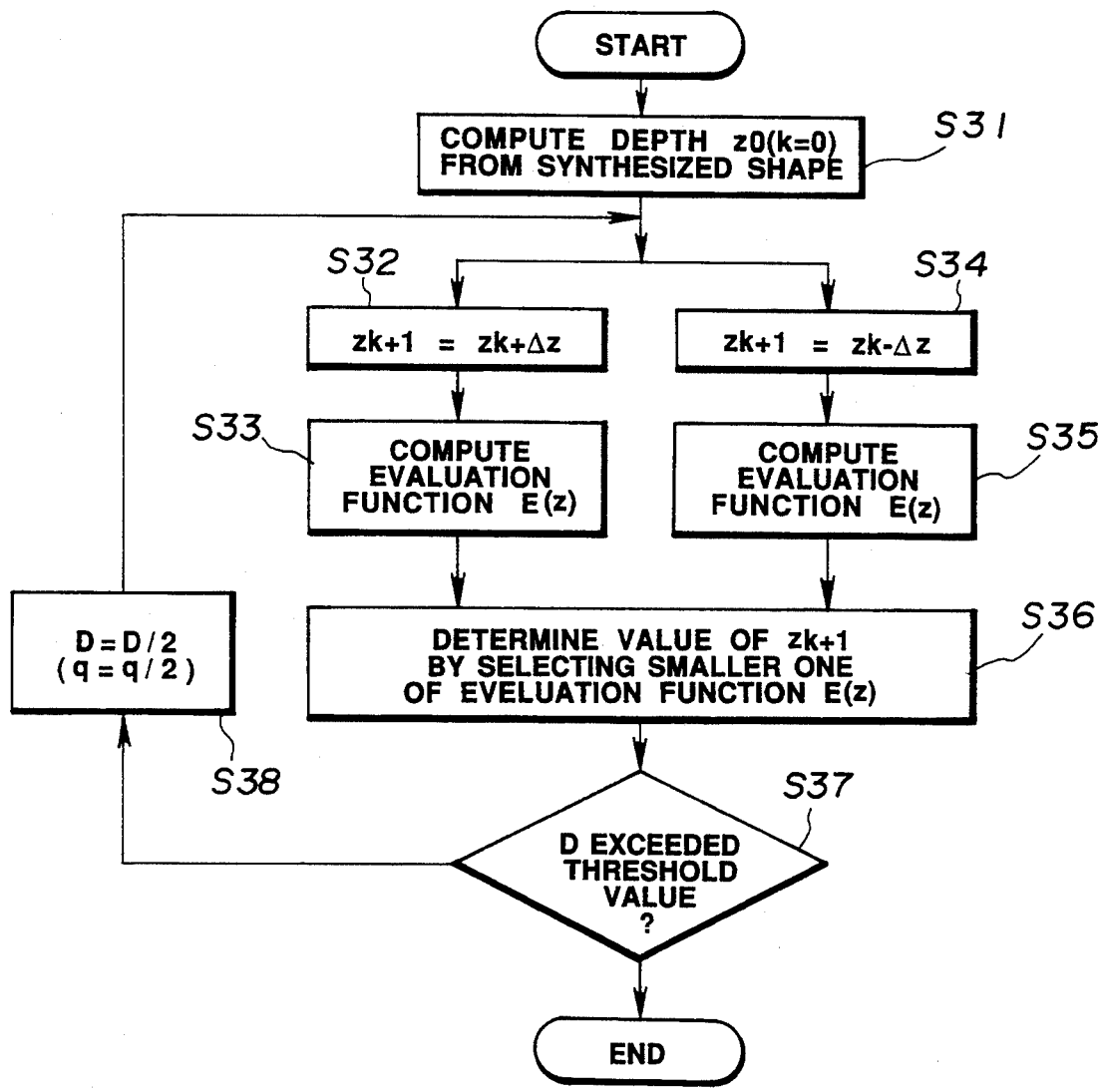
FIG. 18 is a flowchart showing processing for repeatedly estimating a three-dimensional shape.
Figure 19:
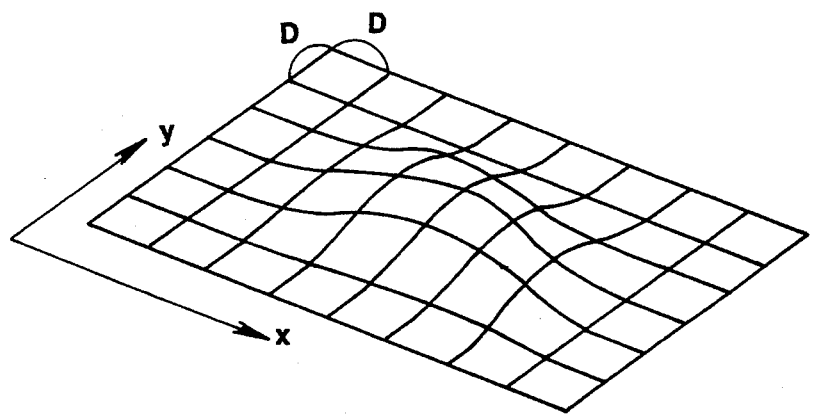
FIG. 19 is a drawing explaining the step of sampling points from the estimated three-dimensional shape at a predetermined interval.
Figure 20A:
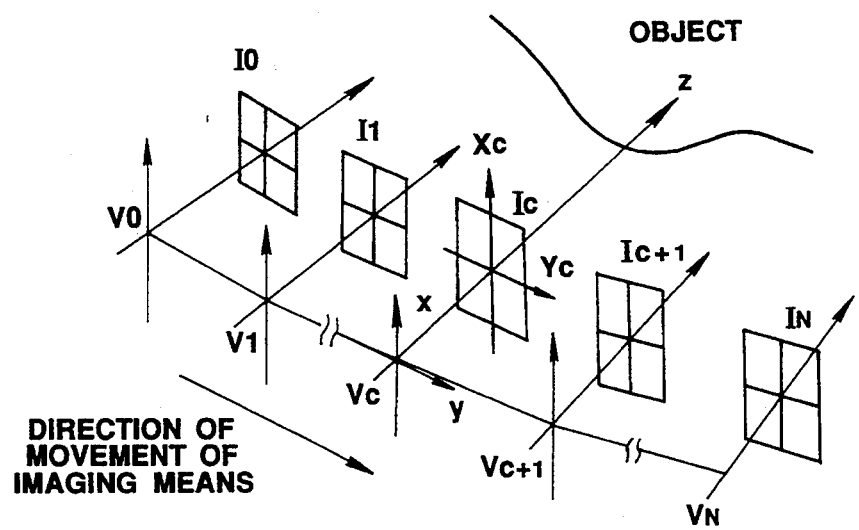
FIGS. 20a and 20b are drawings explaining the relation between an image and an object for determining an evaluation function.
Figure 20B:
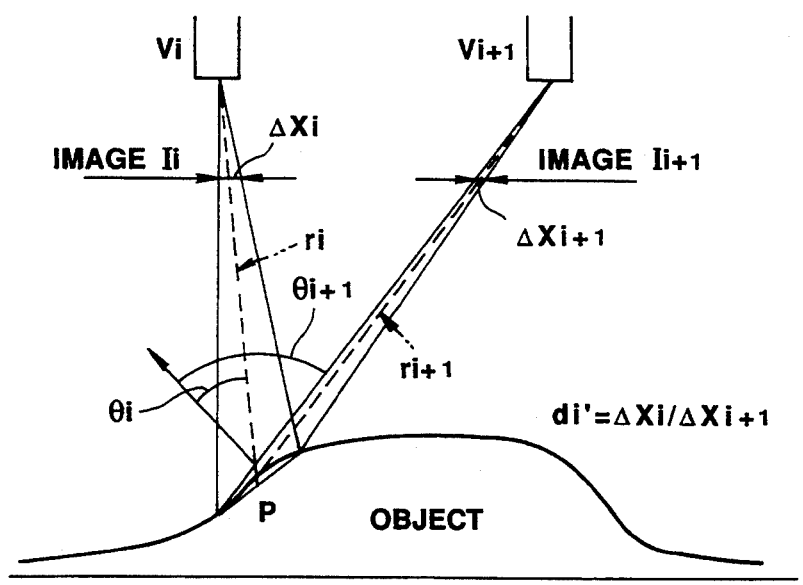

FIG. 18 is a flowchart showing a typical example of repeated processing. In Step S31, points are sampled from the the x, y plane of a three dimensional shape at an interval D, as shown in FIG. 19, and the depth z0 (x, y) from the visual point at each of the lattice points is computed.

In Steps S32 and S34, $+\Delta zk(x,y)$ and $-\Delta zk(x,y)$ are respectively added to the depth $zk(x,y)$ at each lattice point to obtain values $zk(x,y)$. The evaluation functions $E(zk(x,y))$ of the values $zk(x,y)$ are determined in Steps S33 and 35. In Step S36, a smaller evaluation function $E(zk(x,y))$ is selected from the two evaluation functions at each lattice point to obtain a new value $zk(x,y)$.

In Step S37, a decision is made as to whether or not the interval D exceeds a threshold value. If the interval D is smaller than the threshold value, the flow moves to Step S38 in which the interval D is halved, the k value is incremented by one ($k=k+1$), and the depth z is determined again. If the interval exceeds the threshold, the processing is ended. The equation $q=q/2$ in Step S38 will be described below.

The evaluation function is described below.

The evaluation function is defined as the equation (21) below so that the contribution ratio of each image pair (each shift map) to the estimation of a shape is controlled.

$$E(z) = L(z) + \lambda S(z) \quad (\text{wherein } z = z(x,y)) \tag{21}$$

wherein $\lambda$ is a parameter ($k > 0$) controlling the intensity of the second term, and $S(z)$ is a term representing the smoothness of the estimated surface shape and is expressed by secondary partial differentiation of z, as shown below.

$$S(z) = \int\int (zxx^2 + 2zxy^2 + zyy^2)^2 \, dxdy \tag{22}$$

wherein, for example, zxx simply indicates $$\frac{\partial^2 z}{\partial^2 x}.$$

Assuming that N image pairs are present, $L(z)$ is determined. When an image pair Ii–Ij is considered, it is assumed that a target point $P(x,y,z(x,y))$ on an object is projected at points Xi and Xj on images.

The positions of the point Xi and Xj are determined by an estimated value of z. A square difference of the image density values of an areas Wq in the periphery of the point P in the images Ii and Ij is defined by using a window function Wq of a width q as follows:

$$Lijxy(z) = \int \{Ii(Xi - X) - Xi(Xj - X)\}^2 Wr(X) dX \tag{23}$$

If an image of the object surface with the projection position of the point P at the center thereof is not distorted by a difference in the positions of the visual points, and if the image values are not affected, the value of the equation (23) is minimized by the correct z value. When N image pairs are employed, the values of the equation (23) for the image pairs may be added. However, it is thought that when the visual points are greatly separated from each other, the image density value of the same point on the object is also changed.

The image pairs at adjacent visual points only are considered in order to decrease the above influences. In addition, in order to suppress the influences of the image pair at a visual point where the point P cannot be seen, a weight for each image pair is used, the values of the equation (23) is added to determine $Lxy(z)$ as follows:

$$Lxy(z) = \sum_{i=1}^{N} \omega i Li, i+1, xy(z) \tag{24}$$

The value of the equation (24) is determined for the whole estimation area and is indicated by $L(z)$.

$$L(z) = \int\int Lxy(z) dxdy \tag{25}$$

$\omega i$ is a weighting coefficient for each image pair. Considering the fact that the estimation precision generally increases with a decrease in the distance between the imaging means and the object, and that when a difference in the image values of an area is used in the evaluation functions, as in the equation (23), the precision decreases with an increase in distortion between the images, $\omega i$ is expressed by the following equation using the distance ri between each visual point Vi and the estimation point P and the distortion di of a peripheral area of the estimation point P:

$$\omega i = \omega i' / \sum_{k=1}^{N} \omega k' \tag{26}$$

$$(\omega i' = 1/\{di(ri + ri + 1)\})$$

wherein the distortion di is represented by the equation (27) below using a ratio between the lengths DXi and $DXi+1$ of a line with a center at the point P on an object surface when the line is projected on images Ii and $Ii+1$.

$$di = \begin{cases} di' & (di' \geq 1) \\ 1/di' & (di' < 1) \end{cases} \tag{27}$$

$$(di' = \Delta Xi/\Delta Xi + 1)$$

When the object surface is parallel with both images, distortion is absent between the images, and di is the minimum value of 1. When one of the angles qi and $qi+1$ respectively formed by the normal vector of the object surface and the vectors of the visual directions exceeds 90 degrees, the point should be deviated from the images.

An appropriate threshold value (80 degrees in experiment) is thus set so that when one of the angles exceeds the threshold value, wi is considered as zero.

Actual processing for renewing the shape is performed by changing the depth z at the point so as to decrease the $E(z)$ value of the equation (21) while sampling points at an interval D on the x-y plane which showing the object shape by the depth z.

Although the D value must be small in order to correctly determine the shape, since the evaluation function $E(z)$ generally has many local minimum points, the shape is repeatedly renewed by gradually decreasing the depth D and the width q of the window function W (for example, $D=D/2$ and $q=q/2$ as shown in Step S38) in order to prevent convergence at such local points.

In the second embodiment, since repeated estimation is performed by using as an initial value the three-dimensional shape estimated in the first embodiment, a three-dimensional shape with higher precision can be estimated.

A third embodiment is described below.

In this embodiment, processing for estimating again the movement from the shift maps except a shift map of a portion having a high possibility of occlusion, i.e., a shift map having a low wi value, is added to the repeated processing in the second embodiment, thereby improving the precision of the estimation of movement.

Figure 21:
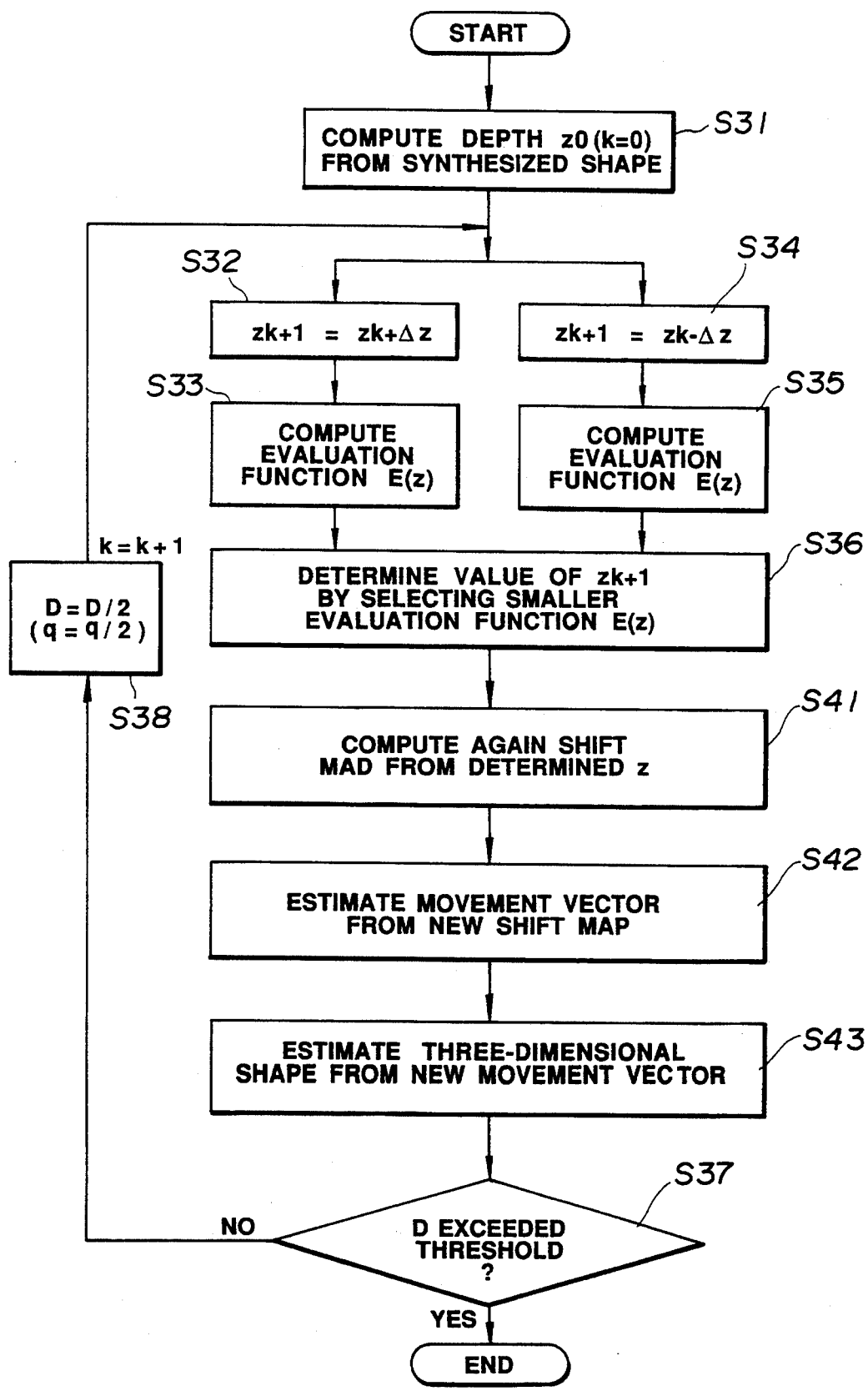
FIG. 21 is a flowchart showing processing for repeatedly estimating a three-dimensional shape in accordance with a third embodiment of the present invention.

FIG. 21 is a typical flowchart showing repeated processing. The steps S31 through S36 in which the evaluation functions E(z) are introduced, and a smaller evaluation function E(z) is selected to determine the value of the depth z at each lattice point are the same as those in the second embodiment. The processing in steps S41 through S43 is interposed between Steps S36 and S37 shown in FIG. 18.

In this embodiment, in next step S41, a position on each of the images is calculated using the depth z determined in Step S36, and the amount of shift from the previous position is determined. The shift amount is added to the previous shift maps to compute new shift maps.

In next step S42, movement vectors are estimated from the computed shift maps while the ratio of contribution to the estimation of the movement vectors according to the determined value of wi. A three-dimensional shape is determined again in Step S43.

A decision is made in Step S37 as to whether or not the interval D exceeds a threshold value. If the interval D is smaller than the threshold value, the flow moves to Step S38 in which the interval D and the width q are halved, and the depth z is determined again. If the interval D exceeds the threshold value, the processing is finished.

Even when occlusion is present, this embodiment permits estimation of a three-dimensional shape with high precision without being influenced by the occlusion.

A fourth embodiment is described below.

In this embodiment, a new three-dimensional shape is estimated from the three-dimensional shapes estimated by the methods of the first to third embodiments, and the two-dimensional image data obtained by moving again the imaging means.

Figure 22:
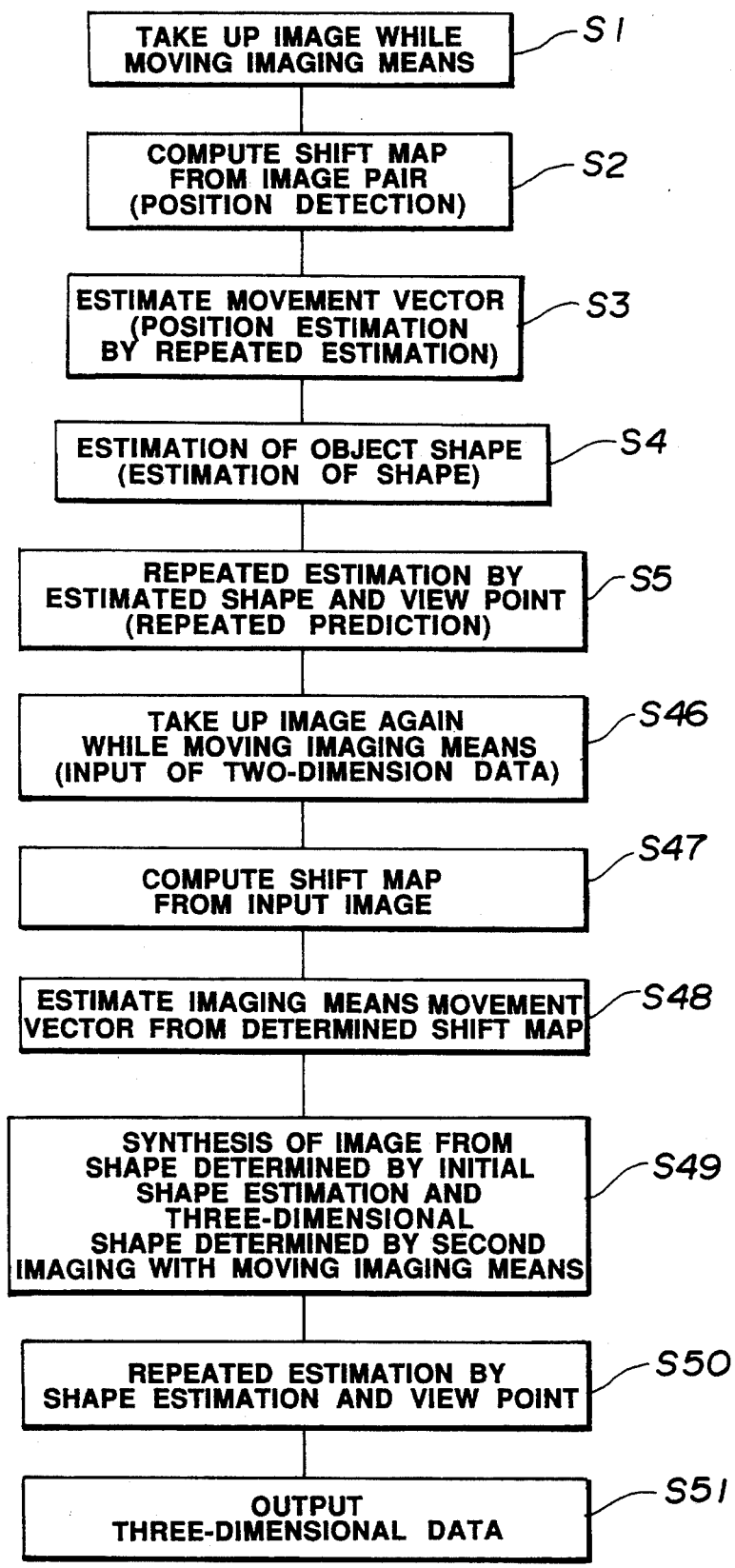
FIG. 22 is a flowchart showing processing contents up to the step of converting two-dimensional image data into three-dimensional image data in accordance with a fourth embodiment of the present invention.
Figure 23:
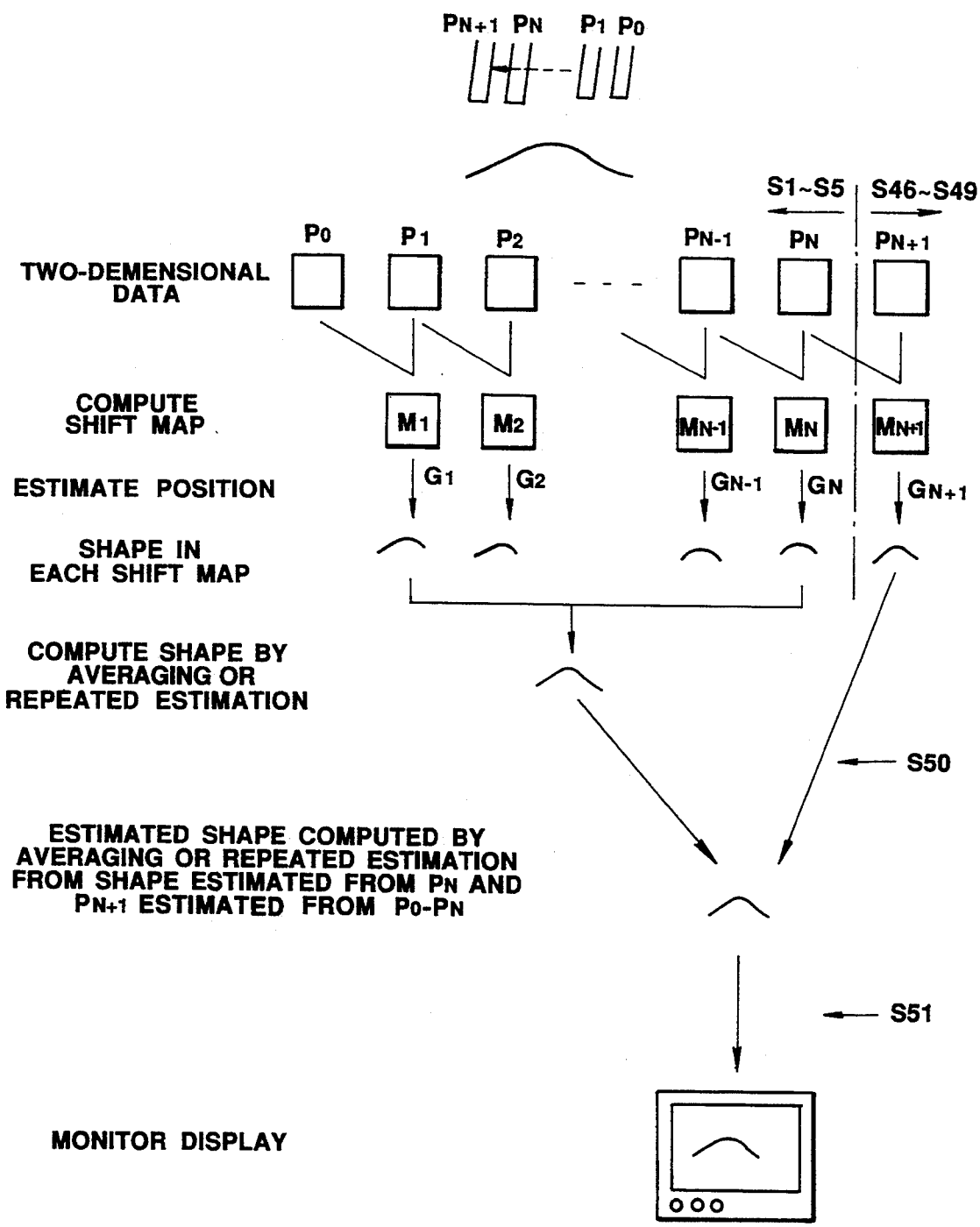
FIG. 23 is a drawing explaining processing contents in accordance with the fourth embodiment.

FIGS. 22 and 23 are respectively a flowchart and a schematic drawing showing the process up to the step of converting two-dimensional image data to three-dimensional image data by the image processing device 3. The process up to the step of computing the three-dimensional data is described below.

In Steps 1 through 5, a three-dimensional shape is estimated from the image data obtained by moving the imaging means by the method employed in each of the first to third embodiments.

In this embodiment, in Step S46 next to Step S5, new two-dimensional image data of different positions are input by moving again the imaging means (the tip of the electronic endoscope 6) little by little relative to the same object.

In Step S47, distortion aberration correction processing is applied to the new plural images obtained in Step S46 for correcting the distortion of the images. Corresponding point tracing is performed for determining the shifts of the corresponding same points using the newest two-dimensional image data obtained in Step S1 and the corrected plural images (image pairs), and shift maps are computed.

In Step S48, the movement vector of the imaging means determined by the method used in Step S3 using the shift maps determined in Step S47. In next Step S49, the distance to the point in each of the images is determined, and the shape of an object is determined for each of the shift maps. A new three-dimensional shape is composed by the three-dimensional shape determined in Step S49 and the three-dimensional shape previously composed in Step S4.

In Step S50, a three-dimensional shape is repeatedly estimated again using the three-dimensional shape estimated in Step S49. The estimated three-dimensional image data is then output to the display device side or the like in Step S51.

A description is made of the processing in Step S46 when two-dimensional image data n+1 is input.

As shown in FIG. 23, a three-dimensional shape is estimated by the method used in each of the first to third embodiments using the first two-dimensional image data to two-dimensional image data n. The two-dimensional image data n+1 is then input while the imaging means (the tip of the electronic endoscope 6) is moved relative to the same object. The obtained two-dimensional image data n+1 is subjected to distortion aberration correction processing for correcting distortion of the images.

The corresponding points are traced between a pair of images n and n+1 to compute a shift map.

The movement vectors of the imaging means between the images n and n+1 are determined from the shift maps. The positional relations between the object and the imaging means are determined by the movement vectors determined.

The positional relations between the object and the imaging means are transformed into the same coordinate space as that of the three-dimensional shape (positional relation between the object and the imaging means) previously obtained in Step S4. A new three-dimensional shape is estimated by averaging the transformed positional relations between the object and the imaging and means and the position of the same point in the three-dimensional shape obtained in Step S4. A new shape can also be estimated by weighting according to the positional relation between the three-dimensional shape and the imaging means and adding the positional relations in place of averaging.

A new three-dimensional shape is repeated estimated again using the estimated three-dimensional shape, and the newly estimated three-dimensional image data is output to the display device side.

When a three-dimensional structure is estimated, it is difficult to search the corresponding points of the images with sufficient precision. It is thus thought to introduce some restriction condition for stably determining a solution. A considerable method is a normalization method.

In the second embodiment, the restriction condition in which the estimated surface shape smoothly changes is introduced by introducing the secondary partial differentiation of z into the second term of the evaluation function E(z) to estimate a three-dimensional shape.

When an image of a part in a living body is formed, as an endoscopic image, it is thought that the three-dimensional structure to be determined generally has a smoothly curved surface. This is thus used as a restriction condition for normalization. When a renewal amount in repeated estimation of a shape is determined, a method can be used in which a correction amount is introduced so as to decrease the differences in shape between the object part and the peripheral portion thereof.

A method other than the secondary partial differentiation used in the second embodiment may be used for determining an actural renewal amount in which the correction amount $\Delta z1$ of the depth derived by the repeated estimation and the correction amount $\Delta z2$ derived as a difference between the depth determined from the information about the depth of the peripheral portion by interpolation and the present depth are weighted and added according to the following equation:

$$\Delta z=(1-\lambda)\Delta z1+\lambda\Delta z2 \qquad (28)$$

The above repeated estimation permits the estimation of a shape with higher precision than that of the shape estimated by a pair of conventional stereotype endoscopic imaging means.

In this embodiment, the amount of image data used for estimating a three-dimensional shape is increased by further imaging an object, thereby enabling the estimation of a three-dimensional shape with higher precision.

The shape data output in each of the above embodiments is computed as a relative value. In order to compute the shape data as an absolute value, one of the parameters related to the movement of the tip (imaging means) of the endoscope is determined as an absolute value (reference length or angle value) so that the size of a shape can be determined as an absolute value by scaling using the absolute parameter as a reference value during computation of the absolute values.

Size determination means for determining a reference size for the movement of the imaging means is thus required. For example, a curvature amount is determined by detecting the rotation of an angle knob in the endoscope operating portion and is used as a parameter, as disclosed in Japanese Patent Publication No. 63-246716. Referring to FIG. 1, the detected curvature amount in the operating portion 12 of the electronic endoscope 6 is sent to the image processing device 3 through the observation device 7, and the absolute value of a shape is computed in the image processing device 3 using the curvature amount detected on the computation of the absolute value.

A method or means for determining a curvature angle from the rotation of the angle knob is described in detail below with reference to FIG. 24.

Figure 24:
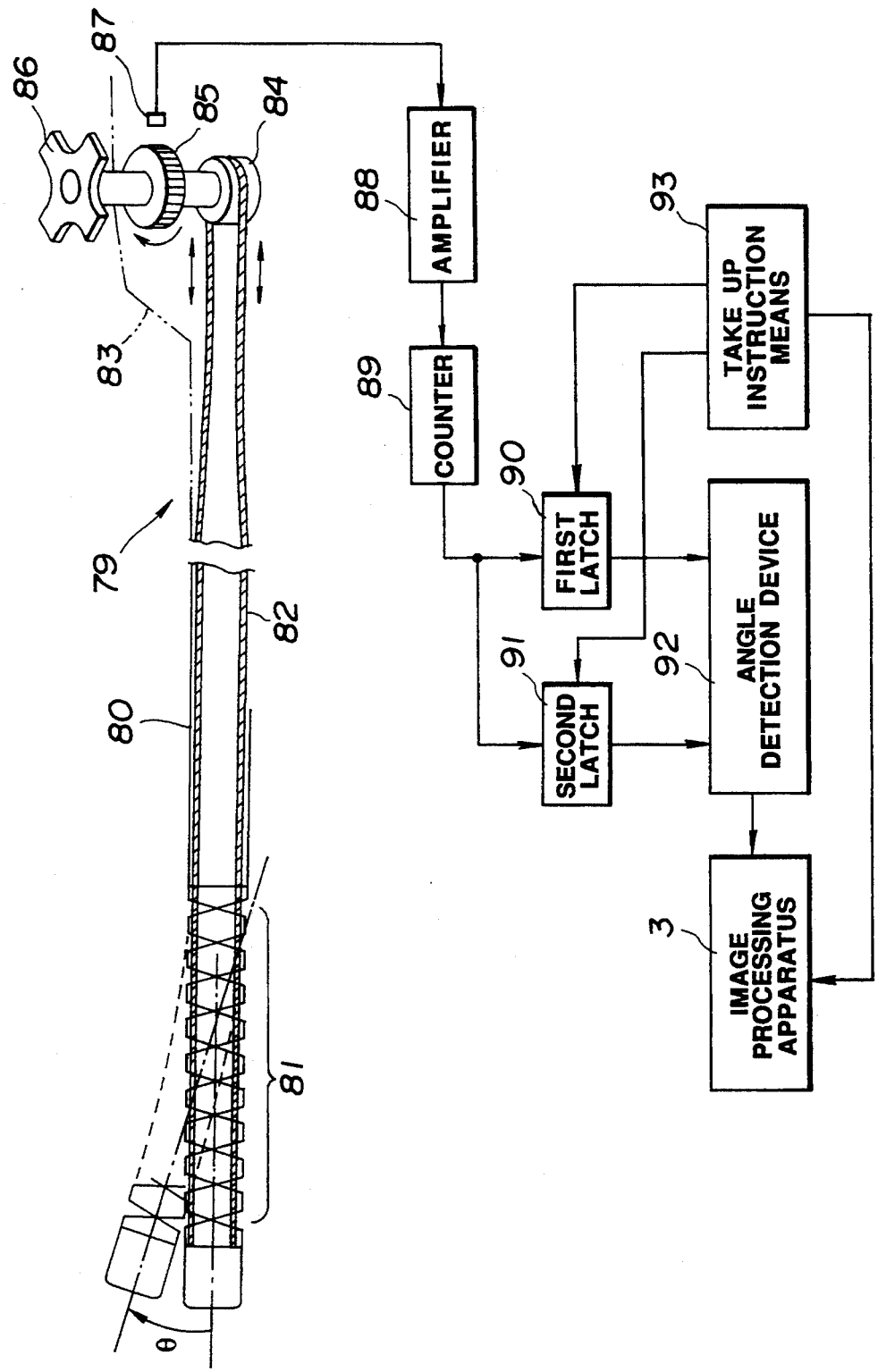
FIG. 24 is a drawing explaining a configuration for obtaining angular information from the rotational amount of an angle nob.

In the endoscope 79 (corresponding to the electronic endoscope 6 shown in FIG. 1) shown in FIG. 24, an angle wire 82 is wound on a rotating drum 84 disposed in an operating portion 83 of the endoscope 79 so as to curve a curved portion 81 provided at the tip of an insertion portion 80. The rotating drum 84 is fixed concentrically with a pattern disk 85 disposed in the operating portion 83 and an angle knob 86 projected from the operating portion 83.

A pattern with white and black lines at equal intervals is formed on the peripheral surface of the pattern disk 85 so as to be read by a sensor 87 comprising a reflection type photosensor or the like. The output of the sensor 87 is input to an amplifier 88, and the output of the amplifier 88 is input to a counter 89.

The output of the counter 89 is input to first and second latches 90 and 91, the output of the latches 90 and 91 is input to an angle detection device 92. The angular information about the curved portion obtained by the angle detection device 92 is sent to the image processing device 3. The output of take-up instruction means 93 comprising an operating switch, a timing circuit and the like is input to the first and second latches 90 and 91 and the image processing device 3.

The curved portion 81 comprises many joint pieces which are rotatably connected to each other so as to be curved to the side on which the angle wire is pulled. A tip portion 94 is formed at the front portion of the curved portion 81, and the illuminating window for emitting illuminating light and an observation window for observation (imaging) are provided on the tip portion 94, as described above with reference to FIG. 1.

The operation is described below. The value of the counter 89 is recorded on the basis of the instruction from the take-up instruction means 93 in a predetermined curvature state. The angle knob 86 is then slightly rotated for moving the curved portion 81 of the endoscope 79. The rotation of the angle knob 86 causes the rotation of the pattern disk 85 and thus the sensor to detect a change in the white and black lines. In other words, a rotational encoder is formed, and the rotational amount of the pattern disk 85 and information about the rotational direction thereof are transmitted to the counter 89 through the amplifier 88. In the state the curved portion, the value of the counter 89 is recorded in the second latch 91.

The values respectively recorded in the first and second latches 90 and 91 are supplied to the angle detection device 92 and converted into angular information q therein. The angular information q is sent to the image processing device 3 and is used for converting the relative positional relation between the object and the imaging means into an absolute value (distance).

Although, in FIG. 24, the angular information q of the imaging means is obtained by rotation of the angle knob, the method of determining an absolute value is not limited to this. For example, a substance having a reference size (for example, a measure or the like) may be projected from the channel at the tip of the endoscope, imaged together with the object and used as a reference value for determining an absolute value.

The positional information may also be obtained by the three-dimensional manipulation below.

Although, the electronic endoscope 6 is used as the imaging means which constitutes the endoscope device 2 in each of the above embodiments, the imaging means is not limited to this, a system having the structure below may be used.

Figure 25:
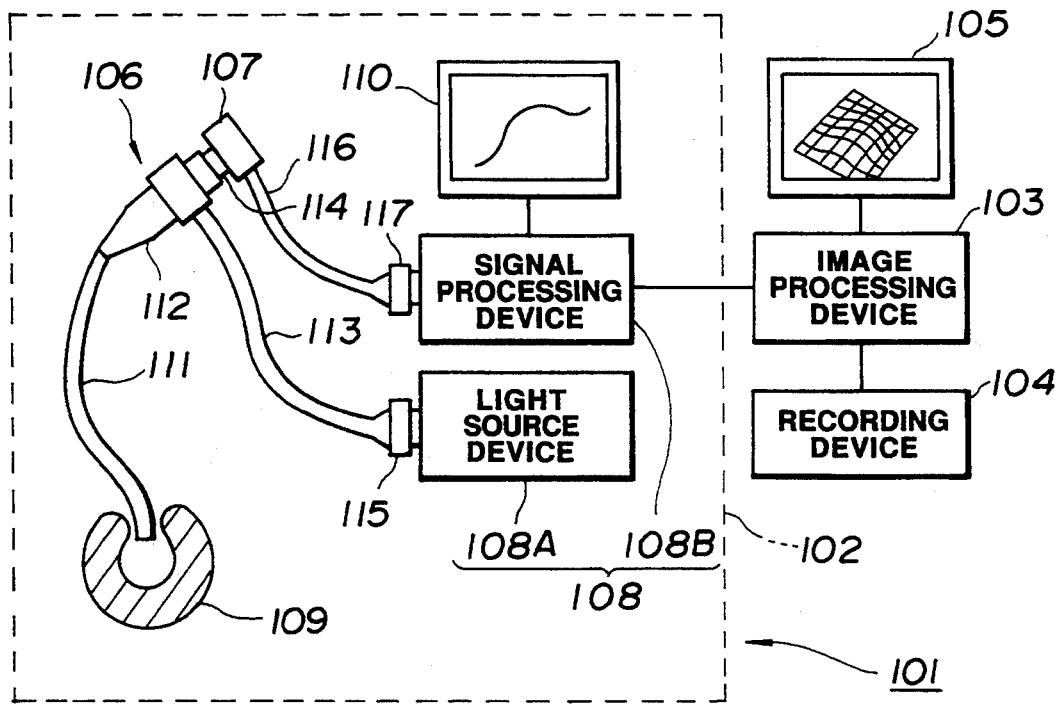
FIG. 25 is a block diagram showing the whole structure of an endoscopic system using a scope with an external TV camera mounted on a fiberscope.

In FIG. 25, a fiber scope 106 and a TV camera 107 mounted on the fiber scope 106 are used in place of the electronic endoscope 6. The endoscopic system 101 shown in FIG. 25 comprises an endoscopic device 102 generating an image signals, an image processing device 103 for processing the image signals output from the endoscopic device 102 to estimate a three-dimensional shape, a recording device 104 and a monitor 105.

The endoscopic device 102 comprises the fiber scope 106 for transmitting optical images of an affected part or the like in a living body 109, the TV camera 107 for converting the optical images into electric signals, a light source device 108A for supplying illuminating light to the fiber scope 106, a signal processing device 108B for processing the electric signals output from the TV camera 107, and an observation monitor 110 for displaying the image signals output from the signal processing device 108B.

The fiber scope 106 comprises a long then insertion portion 111 having flexibility, an operating portion 112 formed at the rear end of the insertion portion 111, a light guide cable 113 extended from the operating portion 112, and an ocular portion 114 formed at the tip of the operating portion 112. The connector 115 provided at an end of the light guide cable 113 can be connected to the light source device 108A.

The TV camera 107 mounted on the ocular portion 114 contains a sensor such as CCD or the like, and a connector 117 provided at an end of a signal cable 116 can be connected to the signal processing device 108B.

The light source device 108A and the signals processing device 108B constitute the observation device 108. The light source device 7A and the signal processing portion 7B used in the first embodiment can be used as the light source device 108A and the signal processing device 108B, respectively. Although, in the first embodiment, color images are formed by a face-sequence illumination method, color images may be formed under white illumination.

For example, the devices 3 and 4 used in the first embodiment can be used as the image processing device 103 and the recording device 104, respectively. The operation and the effect of the system 101 are the same as those of a case using the electronic endoscope 6, e.g., the first embodiment.

Figure 26:
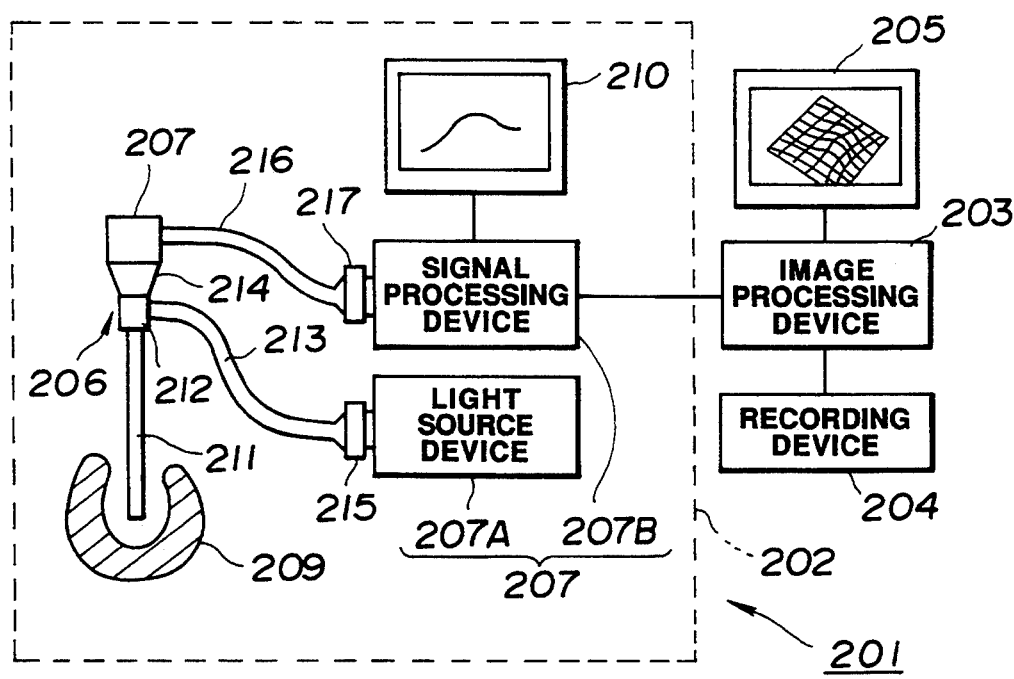
FIG. 26 is a block diagram showing the whole structure of an endoscopic system using a scope with an external TV camera mounted on a hard endoscope.

In FIG. 26, a hard endoscope 206 and a TV camera 207 mounted on the hard endoscope 206 are used in place of the electronic endoscope 6. The endoscopic system 201 shown in FIG. 26 comprises an endoscopic device 202 generating image signals, an image processing device 203 for processing the image signals output from the endoscopic device 202 to estimate a three-dimensional shape, a recording device 204 and a monitor 205.

The endoscopic device 202 comprises the hard endoscope 206 for transmitting optical images of an affected part or the like in a living body 209, the TV camera 207 for converting the optical images into electric signals, a light source device 208A for supplying illuminating light to the hard endoscope 206, a signals processing device 208B for processing the electric signals output from the TV camera 207, and an observation monitor 210 for displaying the image signals output from the signal processing device 208B.

The hard endoscope 206 comprises a long, thin and rigid insertion portion 211, a holding portion 212 formed at the rear end of the insertion portion 211, a light guide cable 213 connected to the hold portion 212, and an ocular portion 214 formed at the tip of the hold portion 212, A connector 215 at an end of the light guide cable 213 can be connected to the light source device 208A.

The TV camera 207 mounted on the ocular portion 214 contains a sensor such as CCD or the like, and a connector provided at an end of a signal cable 216 can be connected to the signal processing device 208B.

The light source device 208A and the signals processing device 208B constitute the observation device 208. The light source device 7A and the signal processing portion 7B used in the first embodiment can be used as the light source device 208A and the signal processing device 208B, respectively. Although, in the first embodiment, color images are formed by a frame-sequence illumination method, color images may be formed under white illumination.

For example, the devices 3 and 4 used in the first embodiment can be used as the image processing device 203 and the recording device 204, respectively.

The operation and the effect of the system 201 are the same as those of a case using the electronic endoscope 6, e.g., the first embodiment.

Figure 27:
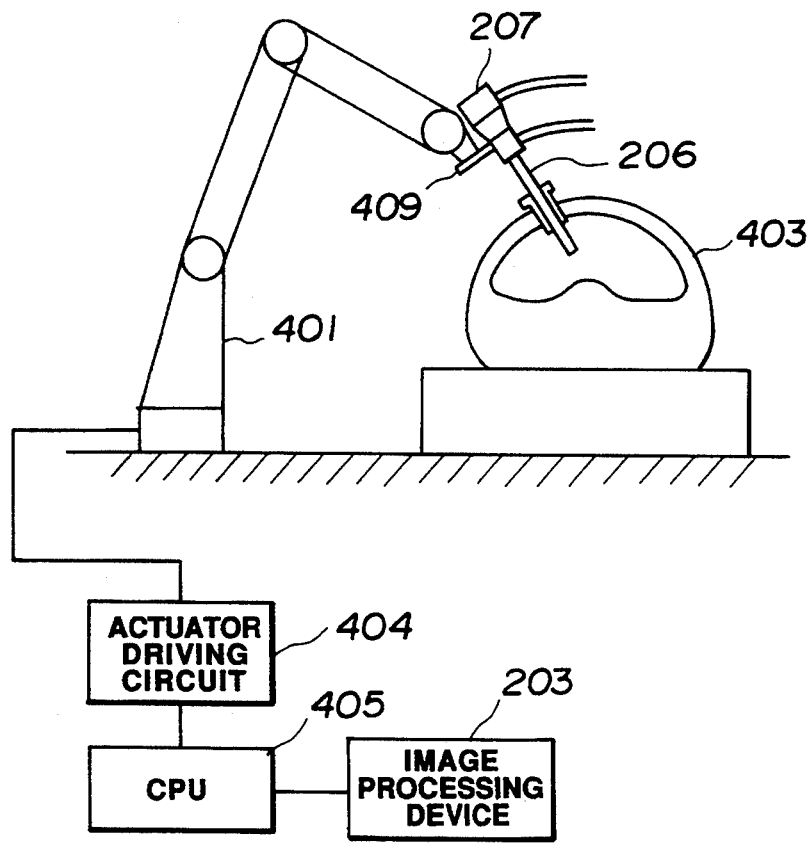
FIG. 27 is a drawing explaining a principal portion of an endoscopic system for obtaining positional information using a three-dimensional manipulator.

In the system 201, for example, positional information may be obtained from a three-dimensional manipulator 401, as shown in FIG. 27.

In the system shown in FIG. 27, the hard endoscope 206 equipped with the TV camera 207 is fitted to the manipulator 401 so that an affected part or the like in a living body 403 is observed while the position of the hard endoscope 206 is detected from the manipulator 401.

The hard endoscope 206 is attached to the top arm provided on the manipulator 401 so that the hard endoscope 206 can be moved to a predetermined position by changing the angle of each of the arms of the manipulator 401.

Each of the arms of the manipulator 401 is moved by the control signal generated from an actuator driving circuit 404 so that the hard endoscope 206 is moved to a predetermined position. A CPU 405 controls the actuator driving circuit 404, and outputs the input positional information of each of the arms to the image processing device 203.

The image processing device 203 receives the positional information of the hard endoscope 206 from the CPU 405 and converts the relative positional relation between the object and the imaging means into an absolute value (distance) on the basis of the positional information received.

An endoscopic system according to a fifth embodiment of the present invention is described below.

Figure 28:
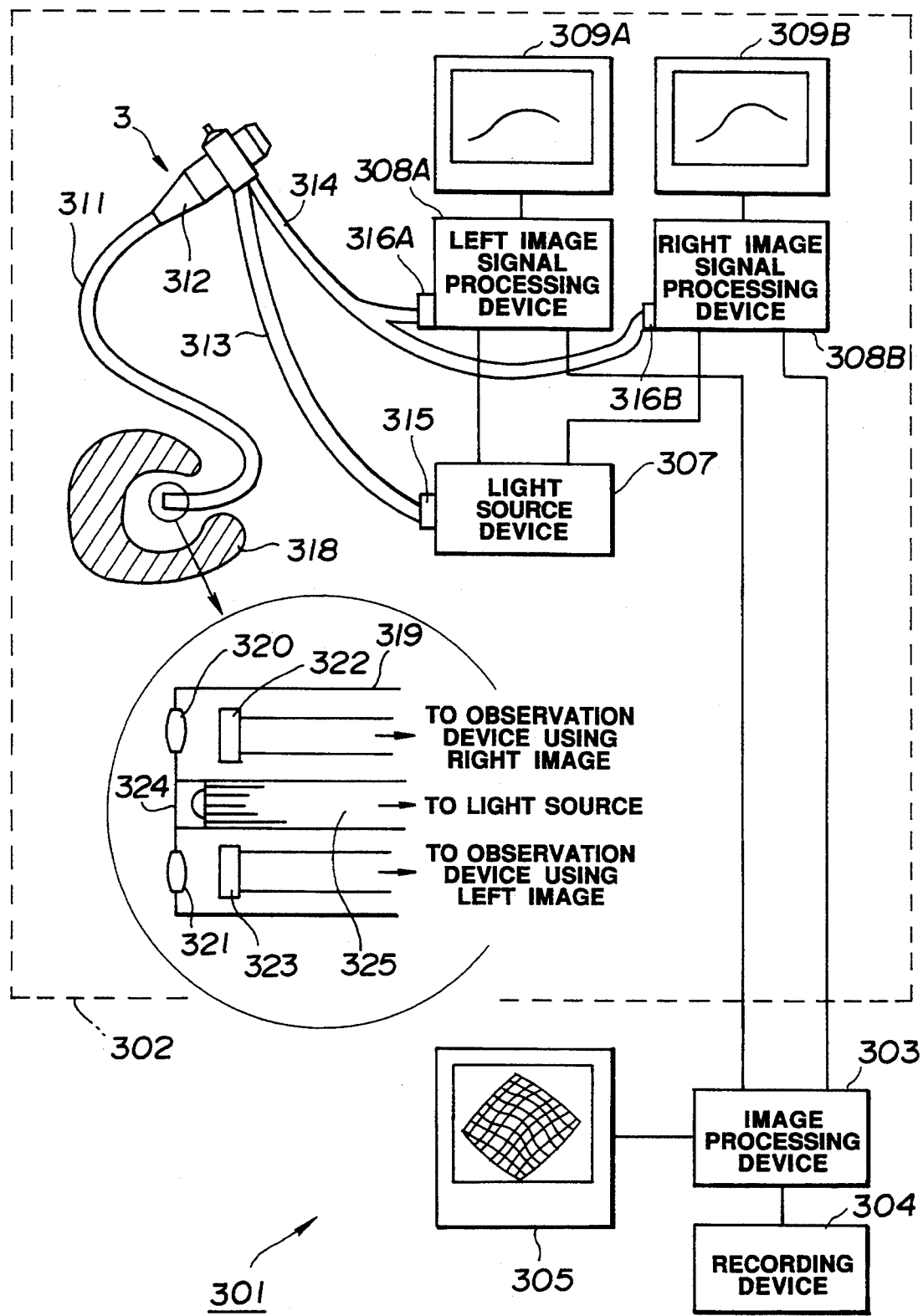
FIG. 28 is a block diagram showing the whole configuration of an electronic endoscopic system in accordance with a fifth embodiment of the present invention.

The endoscopic system 301 shown in FIG. 28 comprises an electronic endoscopic device 302 for imaging the interior of a body cavity, an image processing device 303, a recording device 304 and a monitor 305.

The electronic endoscopic device 302 comprises an electronic endoscope 306 with a compound eye, a light source device 307 for supplying illuminating light to the electronic endoscope 306, a left image signal processing device 308A for processing the left image signal obtained from the electronic endoscope 306, a right image signal processing device 308B for processing the right image signals obtained from the electronic endoscope 306, and observation monitors 309A and 309B for displaying the image signals output from the signal processing devices 308A and 308B, respectively.

The electronic endoscope 306 comprises a long thin insertion portion 311 having flexibility so that it can be inserted into a living body 318, an operating portion 312 provided at the rear end of the insertion portion 311, a light guide cable 313 extended from the operating portion 312, and a universal cable 314.

A connector 315 at an end of the light guide cable 313 is connected to the light source device 307, and an end of the universal cable 314 is branched into two parts at ends of which connectors 316A and 316B are respectively provided. The connectors 316A and 316B are connected to the left image signal processing device 308A and the right image signal processing device 308B, respectively.

On the tip 319 of the insertion portion 311 are provided a plurality of observation windows, for example, two observation windows, and an illumination window. A right eye objective lens system 320 and a left eye objective lens system 321 are respectively provided at positions on the insides of the observation windows so as to have a parallax. Solid state sensors 322 and 323 which each form the imaging means are disposed at the image-formation positions of the objective lens systems 320 and 321, respectively.

A light distribution lens 324 is provided on the inside of the illumination window, and a light guide 325 comprising a fiber band is disposed at the rear end of the light distribution lens 324. The light guide 325 is passed through the insertion portion 311, and the illuminating light is supplied to the incident end of the light guide 325 from the light source device 307.

The illuminating light is transmitted by the light guide 325 and is applied to an object through the front end surface thereof and an objective lens 324. The light reflected from the object forms a right image and a left image in the solid state sensors 322 and 323 by the objective lens systems 320 and 321, respectively.

A description will now be made of the principle of length measurement for calculating the distance between a specified position and the end surface of the endoscope in the electronic endoscope 306 with a compound eye.

Figure 29:
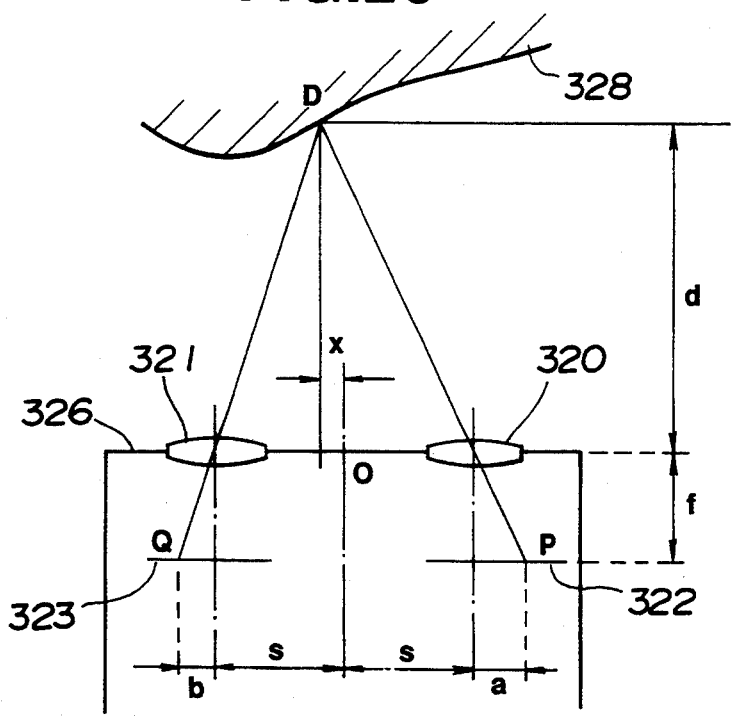
FIG. 29 is a drawing explaining measurement of a length by an electronic endoscope having a compound eye.

In FIG. 29, a point D is a target point on an object 328 in the living body 318, and points P and Q are points on the focal images of the objective lenses 320 and 321 corresponding to the image points in the left image formation means 322 and the right image formation means 323, respectively. A point O is the intersect of the endoscope end surface 326 and the median line between the optical axes of the objective lenses 320 and 321.

It is assumed that the distance between the point D and the endoscope end surface 326 is d, and that a lateral deviation of the median line between the optical axes of the objective lenses 320 and 321 is x.

It is also assumed that the distance between the endoscope end surface 326 and the focal surface of the objective lenses 320 and 321 is f, that the distance between the optical axes of the objective lenses 320 and 321 is 2s, and that the distance between the optical axis of the objective lens 320 and the point P is a, and the distance between the optical axis of the objective lens 321 and the point Q is b.

On the above assumptions, the following equations are established by similarity of a triangle, as shown in FIG. 29:

$$f(s+x) = ad$$

$$f(s-x) = bd$$

If the above two equations are solved for x and d, the following equations are obtained:

$$x = s(a-b)/(a+b)$$

$$d = 2fs/(a+b)$$

Since the values of a, b, f and s are known, the unknown values x and d can be determined.

Figure 30A:
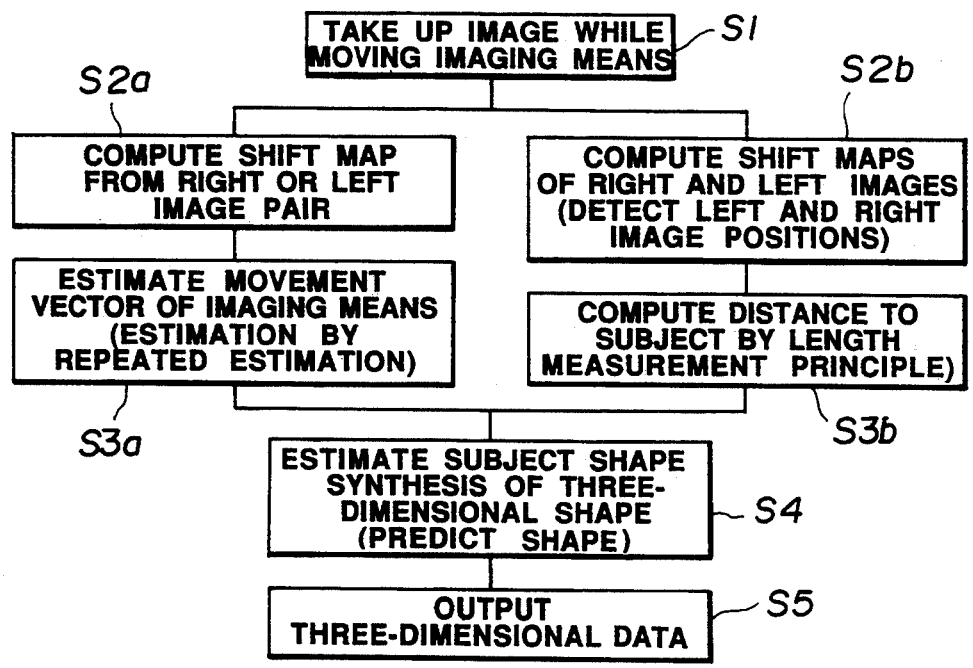
FIGS. 30a and 30b are flowcharts showing processing contents in accordance with the fifth embodiment.
Figure 30B:
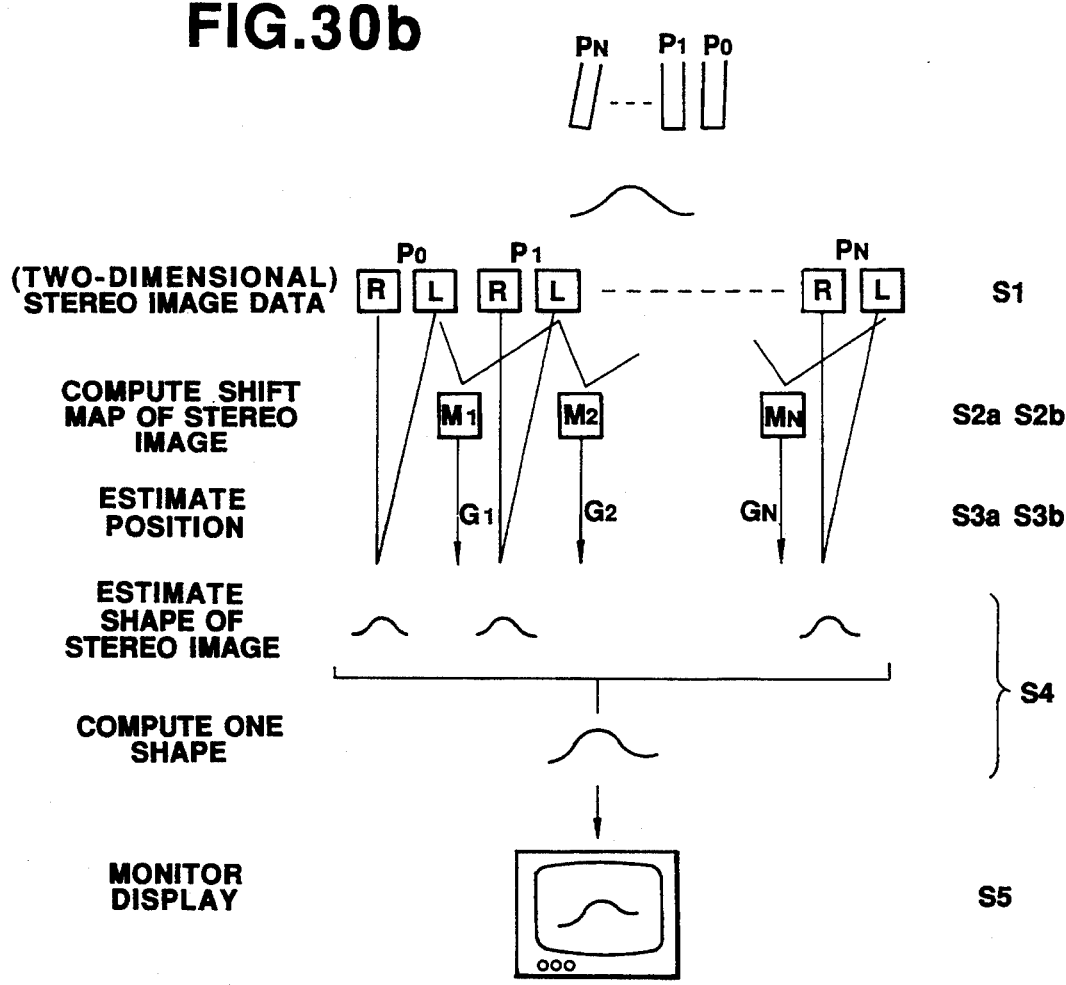

FIGS. 30a and 30b are drawings respectively showing a flow and process up to the step of converting two-dimensional image data into three-dimensional image data by the image processing device 303. The process up to the step of computing the three-dimensional data is described below.

In Step S1, the left and right images formed by moving the imaging means are input to the image processing device 303. Namely, left and right image data at different positions are input while the imaging means (the tip of the electronic endoscope 311) is moved relative to the same object little by little.

In next Step S2a, the plural left and right images obtained in Step S1 are subjected to distortion aberration correction processing for correcting distortion of the images. Corresponding point tracing is performed for the corrected right images or left images (image pairs). Namely, an image (template image) representing the object is selected, and a plurality of points on the selected image are selected and traced along the movement of the selected points to another image (reference image). Shift maps which represent the directions and amount of the movement of the selected points on the template image are formed. FIG. 30b shows the process for forming shift maps of the left images by the same method as that employed in the first embodiment.

In Step S3a, for example, the movement vector of the lift eye imaging means is determined by repeated processing by the method of steepest descent or the like using the left image shift maps determined in Step S2a, and the relative position between the left eye imaging means and the object is determined.

In Step S2b, shift maps of the right and left images of each imaging means obtained in Step S1 are formed by the corresponding point tracing. In this step, the points used for forming the shift maps from the left and right images are the same as those for the shift maps of the left images determined in Step S2a. In Step S3b, the distance between the object and each imaging means is computed using the shift maps formed in Step S2b and the above-described principle of length measurement for a compound eye.

In Step S4, coordinate transformation is made so that the relative position between the imaging means and the object, which is determined by the shift maps of the left images, and the distance between the imaging means and the object, which is determined by the right and left images are indicated in the same coordinate system, and the shape of the object is determined by averaging the distances of the respective same points, which are subjected to coordinate transformation. In Step S5, the estimated three-dimensional image data is output to the display device or the like.

A different embodiment may comprises partial combination of the above embodiments, and the present invention includes such an embodiment.

What is claimed is:

1. An endoscopic image processing device comprising:
   an endoscope provided with imaging means;
   position detection means for detecting the position of the same point on each of a plurality of images of the same object formed by said imaging means at a plurality of imaging positions;
   position estimating means for estimating each position of said object and said imaging means from a shift amount of the position of the same point on each of the images and a rotation matrix and a translation vector calculated using the shift amount;
   shape estimating means for estimating a three-dimensional shape of said object using the positional information of said object and said imaging means which is estimated by said position estimating means; and
   display means for displaying the three-dimensional shape estimated by said shape estimating means.

2. An endoscopic image processing device according to claim 1, further comprising:
repeated processing control means for repeating at least one of a plurality of processes including a first process of detecting the positions of the same point on said plurality of images, a second process of estimating each position of said imaging means and a third process of estimating a three-dimensional shape of said object.

3. An endoscopic image processing device according to claim 1, wherein said position detection means comprises correction means for correcting the aberration caused by an objective light system of said imaging means.

4. An endoscopic image processing device according to claim 1, wherein said position detection means detects the relative position of a point on one of two images to the same point on the other image by setting a first area on one of the two images and detecting a second area on the other of the two images, said second area having substantially the same size as that of said first area and exhibiting the maximum correlation value between images of said first area and said second area.

5. An endoscopic image processing device comprising:
an endoscope provided with imaging means;
position detection means for detecting the position of a single point on each of a plurality of images of a single object formed by said imaging means at a plurality of imaging positions;
position estimating means for estimating each position of said imaging means from the position of the same point on each of the images;
shape estimating means for estimating a three-dimensional shape of said object using the positional information of said imaging means which is estimated by said position estimating means; and
display means for displaying the three-dimensional shape estimated by said shape estimating means,
wherein said position estimating means comprises 8-point algorithm computation means for determining the relative movement of said imaging means to said object by solving for relations between first and second points on said object and which have unknowns as movement parameters of said imaging means resolved into a rotation matrix and a translation vector, using the movement parameters when said first point is moved to said second point by relative movement of said imaging means and when a correspondence between the points of the images respectively formed by projection of said first and second points on a coordinate system of central projection is provided.

6. An endoscopic image processing device according to claim 1, wherein said position estimating means computes the relative positional relation between said imaging means and said object from the results of said computation means.

7. An endoscopic image processing device according to claim 1,
wherein said position estimating means comprises 8-point algorithm computation means for determining the relative movement of said imaging means to said object by solving for relations between first and second points on said object and which have unknowns as movement parameters of said imaging means resolved into said rotation matrix and said translation vector, using the movement parameters when said first point is moved to said second point by relative movement of said imaging means and when a correspondence between the points of the images respectively formed by projection of said first and second points on a coordinate system of central projection is provided, and
wherein said position estimating means computes the relative positional relation by said computation means employing a least squares algorithm for determining the translation vector so as to minimize the relation between said first and second points using the movement parameters of said imaging means, which are resolved in the rotation matrix and the translation vector.

8. An endoscopic image processing device according to claim 7, wherein the relation estimated by said position estimating means is derived on the assumption that the vector connecting the position of said imaging means and said first point, the vector obtained from the vector connecting the position of said imaging means and said second point and said rotation matrix, and said translation vector are present in the same plane.

9. An endoscopic image processing device according to claim 1, wherein said shape estimating means comprises coordinate transformation means for transforming the relations between said object and a plurality of positions of said imaging means into a predetermined coordinate system to compute a three-dimensional shape of said object.

10. An endoscopic image processing device according to claim 9, wherein said shape estimating means computes a three-dimensional shape of said object using a weighting function determined by the relations between the three-dimensional shape of said object obtained by said coordinate transformation means and the imaging positions of said imaging means.

11. An endoscopic image processing device according to claim 9, wherein said shape estimating means comprises repeated estimation means for repeatedly estimating a three-dimensional shape of said object so as to minimize an evaluation function into which a weighting function is introduced, said weighting function being determined from the relationship between a surface shape of said object, a three-dimensional shape of said object and the imaging positions of said imaging means, wherein said surface shape and said three-dimensional shape of said object are estimated by said shape estimating means.

12. An endoscopic image processing device according to claim 11, wherein said evaluation function includes an evaluation value of smoothness of an estimated surface shape of said object.

13. An endoscopic image processing device according to claim 11, wherein said weighting function is determined by an inclination of a surface at a predetermined position of said object and the relative position to said imaging means.

14. An endoscopic image processing device according to claim 11, wherein said repeated estimation means samples points, at a predetermined interval, from the three-dimensional shape of said object estimated by said shape estimation means to compute a three-dimensional shape using said evaluation function for the sampled points, and samples points from the three-dimensional shape obtained at an interval smaller than that of the previous sampling to form a new three-dimensional shape.

15. An endoscopic image processing device according to claim 11, wherein the positions of the same point on the respective images detected by said position detection means from the three-dimensional shape obtained by said repeated estimation means are corrected for again estimating the imaging positions of said imaging means from the corrected detected positions, and a three-dimensional shape of said object is repeatedly estimated again by using the estimated positional information.

16. An endoscopic image processing device according to claim 1, further comprising size determination means for determining a value of a size so that values of a three-dimensional shape of said object are computed with a predetermined scale and displayed.

17. An endoscopic image processing device according to claim 16, said size determination means measures the amount of movement of the tip of said endoscope caused by manual operation of said endoscope.

18. An endoscopic image processing device according to claim 16, wherein said size determination means uses imaging means comprising a plurality of sensors having a known relative positional relation.

19. An endoscopic image processing device according to claim 16, wherein said size determination means has a reference substance having a predetermined size so as to obtain an absolute reference value for said object by imaging said reference substance together with said object and displaying said reference substance on the same place together with said object.

20. An endoscopic image processing device according to claim 1, further comprising a light source device for supplying illuminating light to said endoscope.

21. An endoscopic image processing device according to claim 21, further comprising signal processing means for processing image signals generated from said imaging means.

22. An endoscopic image processing device according to claim 21, further comprising a monitor for displaying the image signals.

23. An endoscopic image processing device according to claim 1, wherein said endoscope has a long thin insertion portion which contains said imaging means at the tip portion thereof.

24. An endoscopic image processing device according to claim 1, wherein said endoscope has a long thin insertion portion in which an image guide for transmitting an optical image is inserted so as to photoelectrically convert an optical image by said imaging means.

25. An endoscopic image processing device according to claim 1, wherein said endoscope has a long thin insertion portion, said imaging means having a plurality of image sensors having the ability of photoelectric conversion being provided at the tip of said insertion portion.

26. An endoscopic image processing device according to claim 1, further comprising repeated processing control means for sequentially repeating at least two of a plurality of processes including a first process for detecting the positions of the same point on said plurality of images, a second process of estimating each position of said imaging means and a third process of estimating a three-dimensional shape of said object.

27. An endoscopic image processing device according to claim 1, wherein said shape estimating means estimates a shape of said object with relative values.

28. An endoscopic image processing device according to claim 1, further comprising reference value detection means for detecting a length or an angle value as a reference so that said shape estimating means estimates a shape of said object with absolute values.

29. An image processing device comprising:
   position detection means for detecting the positions of the same point on respective images formed by imaging means at a plurality of positions of the same object;
   position estimating means for estimating each position of said object and said imaging means from a shift amount of the positions of the same point on said respective images and a rotation matrix and a translation vector calculated using the shift amount;
   shape estimating means for estimating a three-dimensional shape of said object using the positional information of said object and said imaging means estimated by said position estimating means; and
   display means for displaying the three-dimensional shape estimated by said shape estimating means.

30. A method of displaying an endoscopic three-dimensional shape comprising the steps of:
   forming a plurality of images at a plurality of positions on the same object by an endoscope provided with imaging means;
   detecting relative positional deviations of the images by alignment of the positions of the same point on respective images obtained by said image formation step;
   estimating relative movement vectors of said imaging means forming the images on the basis of the information about the relative positional deviations of the images, a rotation matrix and a translation vector using the relative positional deviations of the images, and computing relative positional relations between visual points of said imaging means and said object;
   estimating a three-dimensional shape of said object using the relative positional relations between said visual points and said object; and
   displaying the three-dimensional shape of said object estimated in said shape estimating step on a display device.

31. A display method according to claim 30, further comprising a step of repeating at least one of a plurality of processes including a first process of detecting the positions of the same point on said plurality of images, second process of estimating each position of said imaging means and a third process of estimating a three-dimensional shape of said object.

32. A display method according to claim 30, wherein said positional deviation detection step comprises the step of correcting the aberration caused by an objective optical system of said imaging means.

33. A display method according to claim 30, wherein in said positional deviation detection step, a first area is set on one of two images, and a second area is set on the other image so as to have substantially the same as that of said first area and exhibiting the maximum correlation value between an image in said first area and an image in said second area to detect the positional relation of the same point between the two images.

34. A display method comprising the steps of:
   forming a plurality of images at a plurality of positions on an object by an endoscope provided with imaging means;
   detecting relative positional deviations of the images by alignment of the positions of a single point on respective images obtained by said image formation step;

estimating relative movement vectors of said imaging means forming the images on the basis of the information about the relative positional deviations of the images, and computing relative positional relations between visual points of said imaging means and said object;

estimating a three-dimensional shape of said object using the relative positional relations between said visual points and said object, wherein said position estimating step has a step of computing the relative movement of said imaging means to said object by 8-point algorithm calculation for solving for unknowns as movement parameters of said imaging means, which are resolved into a rotation matrix and a translation vector, and relating a first point to a second point on said object using said parameters when the points on respective images produced by central projection of said first and second points correspond to each other when said first point of said object is moved to said second point by the movement of said imaging means relative to said object.

35. A display method according to claim 30, wherein in said position estimating step, the relative positional relation between said imaging means and said object is computed from the results of said computation step.

36. A display method according to claim 30, wherein said position estimating step has a step of computing the relative movement of said imaging means to said object by 8-point algorithm calculation for solving for unknowns as movement parameters of said imaging means, which are resolved into said rotation matrix and said translation vector, and relating a first point to a second point on said object using said parameters when the points on respective images produced by central projection of said first and second points correspond to each other when said first point of said object is moved to said second point by the movement of said imaging means relative to said object, and wherein in said position estimating step, the positional relation is computed in said computation step using a least squares algorithm determining the translation vector so as to minimize the relation between said first and second points using said movement parameters of said imaging means, which are resolved into the rotation matrix and the translation vector.

37. A display method according to claim 36, wherein said relation used in said position estimating step is derived on the assumption that a vector connecting the position of said imaging means and said first point, a vector determined by a vector connecting the position of said imaging means and said second point and said rotation matrix, and said translation vector are present in the same plane.

38. A display method according to claim 30, wherein said shape estimating step has the coordinate transformation step of coordinate transformation processing for transforming relations of said object and a plurality of points of said imaging means into a predetermined coordinate system to compute a three-dimensional shape of said object.

39. A display method according to claim 38, wherein in said shape estimating step, a three-dimensional step is computed using a weighting function determined by the relations between the three-dimensional shape of said object obtained in said coordinate transformation step and the imaging positions of said imaging means.

40. A display method according to claim 38, wherein said shape estimating step has the repeated estimation step of repeatedly estimating again a three-dimensional shape of said object so as to minimize the evaluation function into which a weighting function determined by the relations between the imaging positions of said imaging means and a surface shape and three-dimensional shape of said object, which are estimated in said shape estimation step, is introduced.

41. A display method according to claim 40, wherein said evaluation function includes an evaluation value of smoothness of the estimated surface shape of said object.

42. A display method according to claim 40, wherein said weighting function is determined by an inclination of the surface at a predetermined position of said object and the relative position between said object and said imaging means.

43. A display method according to claim 40, wherein in said repeated estimation step, points are sampled at a predetermined interval from the three-dimensional shape of said object estimated in said shape estimation step, a three-dimensional shape is computed using the evaluation function for each of the sampled points, and points are sampled from the three-dimensional shape obtained at a interval smaller than that of the previous sampling to obtain a new three-dimensional shape.

44. A display method according to claim 40, wherein the position of the same point detected on each image in said positional deviation detection step is corrected on the basis of the three-dimensional shape obtained in said repeated estimation step, the imaging positions of said imaging means are estimated again from the corrected detected positions, and a three-dimensional shape of said object is repeatedly estimated again using the estimated positional information.

45. A display method according to claim 30, further comprising a size determination step of determining a value of a size, computing a three-dimensional shape of said object with values based on a predetermined scale and displaying the three-dimensional shape computed.

46. A display method according to claim 45, wherein in said size determination step, the movement of the tip of said endoscope caused by a manual operation is measured.

47. A display method according to claim 45, said size determination means uses imaging means having a plurality of sensor having a known relative positional relation.

48. A display method according to claim 45, wherein in said size determination step, a reference substance having a predetermined size is imaged together with said object and displayed on the same screen together with said object to obtain an absolute value of said object.

49. A display method according to claim 30, wherein illuminating light is supplied to said endoscope.

50. A display method according to claim 30, further comprising a signal processing step of processing the signal generated from said imaging means to generate an image signal.

51. A display method according to claim 50, wherein said image signal is display on a monitor.

52. A display method according to claim 30, wherein an optical image transmitted through an image guide for transmitting an optical image produced by said endoscope is subjected to photoelectric conversion in said imaging means.

53. A display method according to claim 30, further comprising a repeated process control step of sequentially repeating at least two of a plurality of processes including a first process of detecting the positions of the same point on said plurality of images, a second process of estimating each position of said imaging means, and a third process of estimating a three-dimensional shape of said object.

54. A display method according to claim 30, wherein in said shape estimation step, a relative shape of said object is estimated.

55. A display method according to claim 30, further comprising a reference value computation step of detecting a length or an angle as a reference so that an absolute value of the shape of said object is estimated in said shape estimation step.

56. An endoscopic image processing device comprising:
  an endoscope provided with imaging means;
  position detection means for detecting the position of a single point on each of a plurality of images of a single object formed by said imaging means at a plurality of imaging positions;
  position estimating means for estimating each position of said imaging means from the position of the same point on each of the images while taking into account any relative movement between said object and said imaging means, said position estimating means comprising 8-point algorithm computation means for determining the relative movement of said imaging means to said object by solving for relations between first and second points on said object and which have unknowns as movement parameters of said imaging means resolved into a rotation matrix and translation vectors, using the movement parameters when said first point is moved to said second point by relative movement of said imaging means and when a correspondence between the points of the images respectively formed by projection of said first and second points on a coordinate system of central projection is provided;
  shape estimating means for estimating a three-dimensional shape of said object using the positional information of said imaging means which is estimated by said position estimating means;
  repeated processing control means for repeating at least one of a plurality of processes including a first process of detecting the positions of the same point on said plurality of images, a second process of estimating each position of said imaging means and a third process of estimating a three-dimensional shape of said object; and
  display means for displaying the three-dimensional shape estimated by said shape estimating means.

* * * * *